(12) United States Patent
Matschiner et al.

(10) Patent No.: US 9,212,208 B2
(45) Date of Patent: Dec. 15, 2015

(54) MUTEINS WITH TEAR LIPOCALIN HAVING AFFINITY TO HUMAN C-MET RECEPTOR TYROSINE KINASE AND METHODS FOR OBTAINING THE SAME

(75) Inventors: Gabriele Matschiner, Munich (DE); Andreas Hohlbaum, Paunzhausen (DE); Martin Huelsmeyer, Wolfersdorf (DE); Stefan Trentmann, Allerhausen (DE)

(73) Assignee: Pieris AG, Freising-Weihenstephan (DE)

( * ) Notice: Subject to any disclaimer, the term of this patent is extended or adjusted under 35 U.S.C. 154(b) by 1447 days.

(21) Appl. No.: 12/865,237

(22) PCT Filed: Jan. 29, 2009

(86) PCT No.: PCT/EP2009/051020
§ 371 (c)(1),
(2), (4) Date: Dec. 21, 2010

(87) PCT Pub. No.: WO2009/095447
PCT Pub. Date: Aug. 6, 2009

(65) Prior Publication Data
US 2011/0098211 A1    Apr. 28, 2011

Related U.S. Application Data

(60) Provisional application No. 61/024,658, filed on Jan. 30, 2008.

(51) Int. Cl.
*A61K 36/00* (2006.01)
*C07K 4/12* (2006.01)
*C07K 14/47* (2006.01)

(52) U.S. Cl.
CPC ..................................... *C07K 14/47* (2013.01)

(58) Field of Classification Search
None
See application file for complete search history.

(56) References Cited

U.S. PATENT DOCUMENTS

2003/0103997 A1 * 6/2003 Boyd .......................... 424/188.1

FOREIGN PATENT DOCUMENTS

WO    WO 2007/107563 A2     9/2007
WO    WO 2007107563 A2 *    9/2007

OTHER PUBLICATIONS

Betts and Russell, Bioinformatics for Geneticists, Ch. 14, Amino Acid Properties and consequences of substitutions, © 2003 John Wiley & Sons, Ltd.*
International Search Report and Written Opinion for PCT/EP2009/051020, dated Jun. 26, 2009, 7 pages.
Ma et al., "c-Met: Structure, functions and potential for therapeutic inhibition," Cancer Metastasis, Dec. 1, 2003, 22(4):309-325.

* cited by examiner

*Primary Examiner* — Christina Bradley
*Assistant Examiner* — Jeanette Lieb
(74) *Attorney, Agent, or Firm* — Foley & Lardner LLP

(57) ABSTRACT

The present invention relates to novel muteins derived from human tear lipocalin having affinity to human c-Met receptor tyrosin kinase (c-Met). The invention also refers to a corresponding nucleic acid molecule encoding such a mutein and to a method for its generation. The invention further refers to a method for producing such a mutein. Finally, the invention is directed to a pharmaceutical composition comprising such a lipocalin mutein as well as to various uses of the mutein.

22 Claims, 6 Drawing Sheets

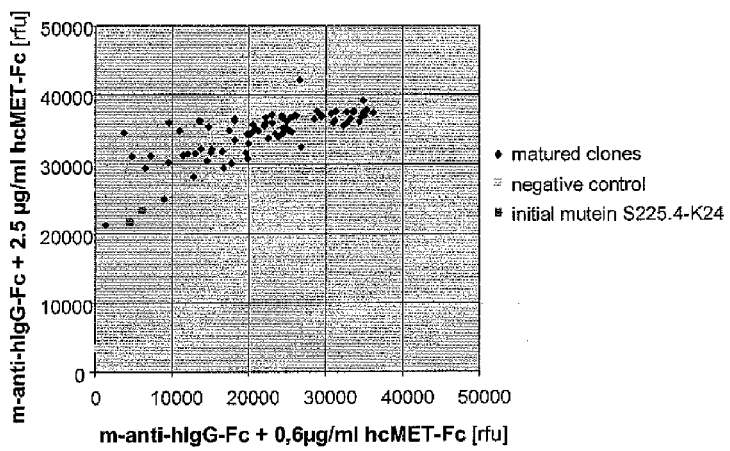

Figure 1A:
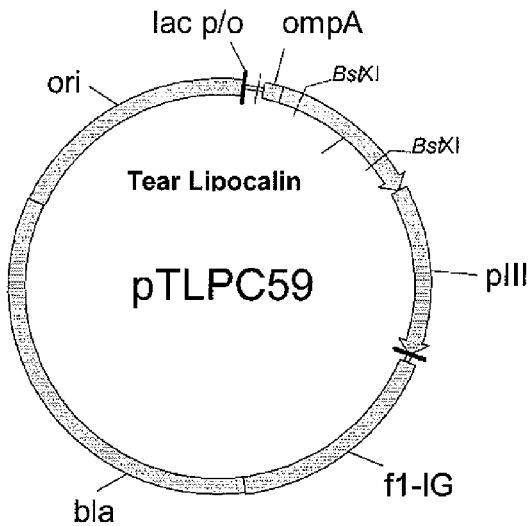

Fig. 9
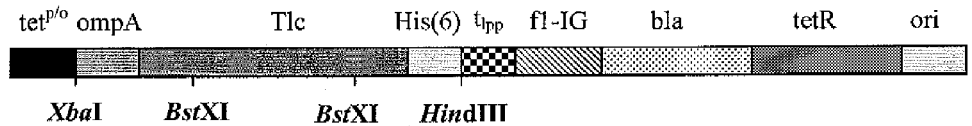
Fig. 10
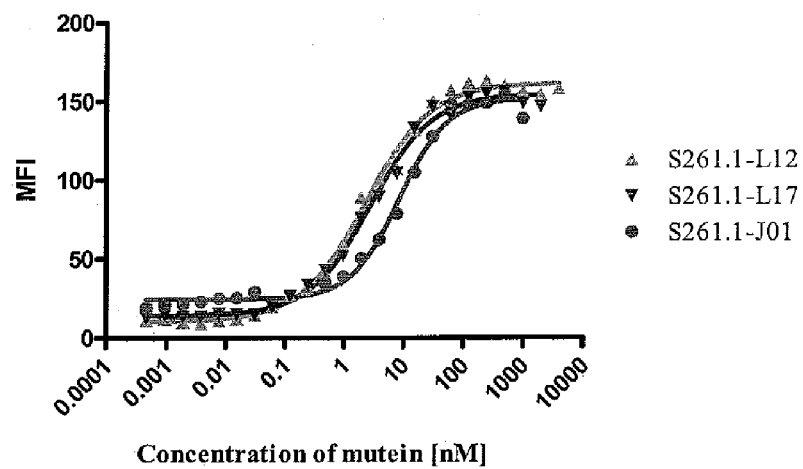
Fig. 11

| Clone | mutated position | Kon [10⁴ M⁻¹s⁻¹] | Koff [10⁻⁴ s⁻¹] | KD [nM] |
|---|---|---|---|---|
| S261.1-L17 |  | 2,01 | 1,17 | 5,8 |
| S275.1-O24 | T26E | 1,97 | 0,521 | 2,7 |
| S275.1-M02 | T26A | 1,94 | 0,57 | 3 |
| S275.1-K22 | T26L | 1,78 | 0,699 | 3,9 |
| S275.2-A20 | Q27S | 1,6 | 0,744 | 4,7 |
| S275.2-K15 | Q27D | 1,76 | 0,41 | 2,4 |
| S275.3-L03 (Dimer) | P29C | 1,71 | 0,166 | 0,97 |
| S275.3-L03 (Monomer) | P29C | 1,65 | 0,302 | 1,8 |
| S275.3-O07 | P29L | 1,45 | 0,91 | 6,3 |
| S275.3-K06 | P29A | 1,47 | 0,878 | 6 |

A) S318.1-C10 (SEQ ID NO:42)
B) S318.1-O12 (SEQ ID NO:49)
C) S318.1-A16 (SEQ ID NO:45)
D) S318.1-I24 (SEQ ID NO:46)
E) S261.1-L17 (SEQ ID NO:34)
F) S318.1-L13 (SEQ ID NO:44)

MUTEINS WITH TEAR LIPOCALIN HAVING AFFINITY TO HUMAN C-MET RECEPTOR TYROSINE KINASE AND METHODS FOR OBTAINING THE SAME

This application is a National Stage application of PCT/EP2009/051020, filed Jan. 20, 2009, which claims the benefit of priority of U.S. provisional application No. 61/024,658 filed Jan. 30, 2008 the contents of which are hereby incorporated by reference in their entirety for all purposes.

The present invention relates to a mutein of human tear lipocalin (hTLc) having detectable binding affinity to the human Met receptor tyrosin kinase (c-Met) or a domain or fragment thereof. Such a mutein comprises amino acid replacements at least one of the sequence position corresponding to sequence positions 26-34, 56-58, 80, 83, 104-106, and 108 of hTLC. The invention also relates to corresponding nucleic acid molecules encoding such a mutein and to a method for their generation. The invention further relates to a method for producing such a mutein. Finally, the invention is directed to a pharmaceutical composition comprising such a lipocalin mutein as well as to various uses of the mutein.

The Met receptor tyrosine kinase (RTK) was first identified as the product of a human oncogene, Tpr-Met (Park et al., Proc. Natl. Acad. Sci, USA, Vol. 84, pages 6379-6383, 1987). The ligand for c-Met was identified as hepatocyte growth factor (HGF). HGF was originally identified as a mitogen for hepatocytes in culture. HGF is identical to scatter factor (SF), a fibroblast-derived factor that promotes dispersal of sheets of epithelial cells, as well as branching tubulogenesis of epithelia grown in three-dimensional cultures. HGF/SF is thus a unique growth factor that elicits multiple cellular responses including mitogenesis, cell motility and morphogenesis.

HGF/SF and c-Met are expressed in many tissues in the adult. The c-Met protein is expressed mostly in epithelial cells, but also in endothelial cells, neural cells, hepatocytes, hematopoietic cells, melanocytes. c-Met might well be one of the most important membrane receptors. Its activation plays a key role in cellular physiology: mitogenesis, motogenesis, morphogenesis. HGF/SF seems essentially produced by cells of mesenchymal origin.

When HGF/SF activates c-Met, the first proteins to be activated downstream are Grb2 (growth factor receptor bound protein 2) and Gab 1 (growth factor receptor bound protein 2 associated binder 1). Grb2 in turn may activate a number of kinase pathways, including the pathway from Ras to Raf to Mek and to MAPK (mitogen-activated protein kinase). Gab 1 activates PI3K (phosphoinositide 3 kinase), which activates STAT3 (signal transducer and activator of transcription). c-Met activation also induces activation of beta catenin, a key component of the wnt pathway which translocates into the nucleus and participates in transcription regulation.

The HGF/c-Met pathway plays an important role in the development of cancer. First through the activation of key oncogenic pathways (Ras, PI3K/STAT3, beta catenin), secondly through endothelial cell proliferation (neoangio genesis), thirdly through increased protease production and hence cell dissociation leading to metastasis.

Various new therapeutic approaches, some of them in phase I or II clinical trials are aimed at the HGF/c-Met pathway. These approaches include anti HGF monoclonal antibodies such the humanized form AV299 of AVEO or a fully human antibody named AMB102 one from Amgen (AMG102). Another approach is the use of truncated variants of c-Met that act as decoys. One such example is the truncated version called CGEN241 from COMPUGEN. Also protein kinase inhibitors (small molecules) that block c-Met induced pathways are used for therapeutic purpose. Examples of such small molecule protein kinase inhibitors include ARQ197 from ARQULE, XL880 from EXELIXIS, SGX523 from SGX Pharmaceuticals, MP470 from SUPERGEN, or PF2341066 from PFIZER However, it would still be desirable to have further compounds available that bind c-Met and that can for example be used for therapeutic purposes.

Accordingly, it is an object of the invention to provide human tear lipocalin muteins having high binding affinity for a given target.

This object is accomplished, for example, by a human tear lipocalin (hTlc) mutein having detectable binding affinity to a human Met receptor tyrosin kinase (c-Met) or a domain or fragment thereof, wherein such a mutein comprises an amino acid replacement at least one of the sequence position corresponding to sequence positions 26-34, 56-58, 80, 83, 104-106, and 108 of hTLC.

In a related aspect, the present invention provides a method for the generation of a mutein of human tear lipocalin, wherein the mutein binds c-Met with detectable binding affinity. This method includes:
(a) subjecting a nucleic acid molecule encoding a human tear lipocalin to mutagenesis at at least one codon of any of the amino acid sequence positions 26-34, 56-58, 80, 83, 104-106 and 108 of the linear polypeptide sequence of native mature human tear lipocalin, wherein at least one of the codons encoding cysteine residues at sequence positions 61 and 153 of the linear polypeptide sequence of the mature human tear lipocalin has been mutated to encode any other amino acid residue, thereby obtaining a plurality of nucleic acids encoding muteins of human tear lipocalin,
(b) expressing the one or more mutein nucleic acid molecule(s) obtained in (a) in an expression system, thereby obtaining one or more mutein(s), and
(c) enriching the one or more mutein(s) obtained in step (b) and having detectable binding affinity for Met by means of selection and/or isolation.

In this context it is noted that the inventors have surprisingly found that removal of the structural disulfide bond (on the level of a respective naïve nucleic acid library) of wild type tear lipocalin that is formed by the cystein residues 61 and 153 (cf. Breustedt, et al. (2005), The 1.8-Å crystal structure of human tear lipocalin reveals an extended branched cavity with capacity for multiple ligands. *J. Biol. Chem.* 280, 484-493) provides tear lipocalin muteins that are not only stably folded but in addition are also able to bind a given non-natural ligand with affinity in the low picomolar range.

The term "mutagenesis" as used herein means that the experimental conditions are chosen such that the amino acid naturally occurring at a given sequence position of human tear lipocalin (Swiss-Prot data bank entry P31025) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the invention. In one exemplary embodiment of the invention, an insertion of several mutations may be introduced into the loop AB of the chosen lipocalin scaffold (cf. International Patent Application WO 2005/019256 which is incorporated by reference its entirety herein). The term "random mutagenesis" means that no predetermined single amino acid (mutation) is present at a certain sequence position but that at least two amino acids can be incorporated with a certain probability at a predefined sequence position during mutagenesis.

The coding sequence of human tear lipocalin (Redl, B. et al. (1992) *J. Biol. Chem.* 267, 20282-20287) is used as a starting point for the mutagenesis of the peptide segments selected in the present invention. For the mutagenesis of the recited amino acid positions, the person skilled in the art has at his disposal the various established standard methods for site-directed mutagenesis (Sambrook, J. et al. (1989), supra). A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of a mutein. It is also possible, as described by Wang, L., et al. (2001) *Science* 292, 498-500, or Wang, L., and Schultz, P. G. (2002) *Chem. Comm.* 1, 1-11, to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2'deoxyguanosine or 6(2-deoxy-β-D-ribofuranosyl)-3,4-dihydro-8H-pyrimindo-1,2-oxazine-7-one (Zaccolo et al. (1996) *J. Mol. Biol.* 255, 589-603), is another option for the introduction of mutations into a chosen sequence segment.

A further possibility is the so-called triplet-mutagenesis. This method uses mixtures of different nucleotide triplets, each of which codes for one amino acid, for incorporation into the coding sequence (Virnekäs B, Ge L, Plückthun A, Schneider K C, Wellnhofer G, Moroney S E. 1994 Trinucleotide phosphoramidites: ideal reagents for the synthesis of mixed oligonucleotides for random mutagenesis. *Nucleic Acids Res* 22, 5600-5607).

One possible strategy for introducing mutations in the selected regions of the respective polypeptides is based on the use of four oligonucleotides, each of which is partially derived from one of the corresponding sequence segments to be mutated. When synthesizing these oligonucleotides, a person skilled in the art can employ mixtures of nucleic acid building blocks for the synthesis of those nucleotide triplets which correspond to the amino acid positions to be mutated so that codons encoding all natural amino acids randomly arise, which at last results in the generation of a lipocalin peptide library. For example, the first oligonucleotide corresponds in its sequence—apart from the mutated positions—to the coding strand for the peptide segment to be mutated at the most N-terminal position of the lipocalin polypeptide. Accordingly, the second oligonucleotide corresponds to the non-coding strand for the second sequence segment following in the polypeptide sequence. The third oligonucleotide corresponds in turn to the coding strand for the corresponding third sequence segment. Finally, the fourth oligonucleotide corresponds to the non-coding strand for the fourth sequence segment. A polymerase chain reaction can be performed with the respective first and second oligonucleotide and separately, if necessary, with the respective third and fourth oligonucleotide.

The amplification products of both of these reactions can be combined by various known methods into a single nucleic acid comprising the sequence from the first to the fourth sequence segments, in which mutations have been introduced at the selected positions. To this end, both of the products can for example be subjected to a new polymerase chain reaction using flanking oligonucleotides as well as one or more mediator nucleic acid molecules, which contribute the sequence between the second and the third sequence segment. In the choice of the number and arrangement within the sequence of the oligonucleotides used for the mutagenesis, the person skilled in the art has numerous alternatives at his disposal.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning (Sambrook, J. et al. (1989), supra). For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

The term "human tear lipocalin" as used herein to refer to the mature human tear lipocalin which is deposited with the SWISS-PROT Data Bank under Accession Number P31025 and the amino acid sequence of which is indicated in SEQ ID NO: 36 here.

In one embodiment of the invention, the method for the generation of a mutein of human tear lipocalin includes mutating at least 2, 3, 4, 5, 6, 8, 10, 12, 14, 15, 16, or 17 of the codons of any of the amino acid sequence positions 26-34, 56-58, 80, 83, 104-106, and 108 of the linear polypeptide sequence of mature human tear lipocalin. In another embodiment all 18 of the codons of amino acid sequence positions 26, 27, 28, 29, 30, 31, 32, 33, 34, 56, 57, 58, 80, 83, 104, 105, 106, and 108 of the linear polypeptide sequence of mature human tear lipocalin are mutated. Accordingly, a Met binding mutein of the invention may comprise a mutation at any of 2, 3, 4, 5, 6, 8, 10, 12, 14, 15, 16, 17 or 18 of the positions of the amino acid sequence positions 26-34, 56-58, 80, 83, 104-106, and 108 of the linear polypeptide sequence of mature human tear lipocalin. However, it is clear to the person skilled in the art that subjecting a sequence position to mutagenesis does not necessarily mean that the chosen possible amino acid replacement will indeed occur in a mutein of the invention. Due to back mutations or structure-function relationship an amino acid residue of the wild type tear lipocalin sequence may also be retained in a mutein of the invention.

In another aspect, the present invention includes a method for the generation of a mutein of human tear lipocalin, wherein the mutein binds c-Met as given non-natural ligand of human tear lipocalin with detectable binding affinity, including:
(a) subjecting a nucleic acid molecule encoding a human tear lipocalin to mutagenesis at at least one codon of any of the amino acid sequence positions 34, 80, and 104 of the linear polypeptide sequence of mature human tear lipocalin, thereby obtaining a plurality of nucleic acids encoding muteins of human tear lipocalin,
(b) expressing the one or more mutein nucleic acid molecule(s) obtained in (a) in an expression system, thereby obtaining one or more mutein(s), and
(c) enriching the one or more mutein(s) obtained in step (b) and having detectable binding affinity for c-Met as given non-natural ligand of human tear lipocalin by means of selection and/or isolation.

In one embodiment of the afore-mentioned method, additionally at least 2, 3, 4, 5, 6, 8, 10, 12, 14, or 15 of the codons of any of the amino acid sequence positions 26-33, 56-58, 83, 105-106, and 108 of the linear polypeptide sequence of mature human tear lipocalin are mutated.

In a further embodiment of the invention, the methods according to the invention include the mutation of both of the codons encoding cysteine at positions 61 and 153 in the linear polypeptide sequence of mature human tear lipocalin. Both positions can for example, be mutated to encode a serine residue.

In another embodiment of the invention as described herein, the codons encoding amino acid sequence positions 111 and/or 114 of the linear polypeptide sequence of mature human tear lipocalin are mutated to encode for example a proline at position 111 and a tryptophane at position 114.

Another embodiment of the methods of the invention involves mutagenesis of the codon encoding the cysteine at position 101 of the linear polypeptide sequence of mature human tear lipocalin so that this codon encodes any other amino acid. In one embodiment the mutated codon encoding position 101 encodes a serine. Accordingly, in some embodiments either two or all three of the cystein codons at position 61, 101 and 153 are replaced by a codon of another amino acid.

According to the method of the invention a mutein is obtained starting from a nucleic acid encoding human tear lipocalin. Such a nucleic acid is subjected to mutagenesis and introduced into a suitable bacterial or eukaryotic host organism by means of recombinant DNA technology. Obtaining a nucleic acid library of tear lipocalin can be carried out using any suitable technique that is known in the art for generating lipocalin muteins with antibody-like properties, i.e. muteins that have affinity towards a given target. Examples of such combinatorial methods are described in detail in the international patent applications WO 99/16873, WO 00/75308, WO 03/029471, WO 03/029462, WO 03/029463, WO 2005/019254, WO 2005/019255, WO 2005/019256, WO 2006/56464, or International patent application PCT/EP2007/057971 the disclosure of which is fully incorporated by reference herein for instance. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) supra; Lowman, H. B. (1997) supra or Rodi, D. J., and Makowski, L. (1999) supra), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755 or the methods specifically described in WO 99/16873, WO 00/75308, WO 03/029471, WO 03/029462, WO 03/029463, WO 2005/019254, WO 2005/019255, WO 2005/019256, WO 2006/56464 or International patent application PCT/EP2007/057971 the disclosure of which is fully incorporated by reference herein for instance.

In accordance with this disclosure, step (c) of the method of obtaining a c-Met binding tear lipocalin mutein further comprises in another embodiment of the above methods:
(i) providing c-Met or a domain or fragment thereof as a given ligand,
(ii) contacting the plurality of muteins with said ligand in order to allow formation of complexes between said ligand and muteins having binding affinity for said ligand, and
(iii) removing muteins having no or no substantial binding affinity.

For the generation of c-Met binding tear lipocalin muteins, any portion (for example, a fragment or single domain) of the extracellular domains of the human Met receptor tyrosin kinase (c-Met) or the entire extracellular domains (that comprises the N-terminal amino acid residues 1 Methione Threonine 932 of the mature entire receptor (SWISS Prot: P08581) can be contacted with (the plurality) of muteins that have been obtained from the expression of the (naïve) nucleic acid library that encodes these muteins. It is possible to use the commercially available extracellular domains that, for example are provided as residues 1-932 fused to a Fc region of a human IgG via a polypeptide linker, for example (R & D Systems, USA, catalog number 358-MT). Further examples of fragments of c-Met that can be used for obtaining muteins described here include, but are not limited to a fragment consisting of the residues 25 to 567 of Met as described in Stamos et al., The EMBO Journal Vol. 23, No. 12, 2004, pages 2325-2335 that contain the seven Sema Domains, or larger fragments that comprise residues 25 to 567. Fragments binding the SEMA domain can be used, if the muteins of the invention are supposed to compete with binding of HGF to the Sema domains. Such muteins may (but do not necessarily have to have, see examples) antagonists of HGF. It is also possible to use fragments such as the one comprising residues 568 to 932, if binding to the Sema Domains is to be avoided. Screening can also be carried out using fragments or other domains such as the PSI domain or the IgG-like domains of c-Met. It is also possible to use for screening purposes, for example, the homolog of the common chimpanzees (pan troglodytes, 99% identity to human c-Met), the macaca homolog (macaca mulatta, 98% identity), the canine ortholog (canis familiaris, 88% identity), the mouse ortholog (SWISS Prot: A1A597, 87% identity) or the rat ortholog (rattus norvegicus, 86% identity) instead of the (extracellular domains of) human c-Met. Such an approach could for example be taken, if muteins having cross-reactivity between the human and the mouse or the rat ortholog (or extracellular domains, for example) would be desired. As it is clear from the above, it is possible to generate in the present invention muteins of tear lipocalin that may have an antagonist action in relation to HGF. Alternatively, the muteins may have a respective non-antagonistic binding mode (cf., Examples in this regard).

In one embodiment of the method of the invention, the selection in step (c) is carried out under competitive conditions. Competitive conditions as used herein means that selection of muteins can encompass at least one step in which the muteins and the given non-natural ligand of human tear lipocalin (target) are brought in contact in the presence of an additional ligand such as HGF, which competes with binding of the muteins to the target. This additional ligand may be a physiological ligand of c-Met such as HGF or any other non-physiological ligand of the c-Met such as an anti-c-Met antibody or a small molecule protein tyro sin kinase inhibitor that binds at least an overlapping or partly overlapping epitope to the epitope recognized by the muteins of the invention and thus interferes with target binding of the muteins. Alternatively, this additional ligand may compete with binding of the muteins by complexing an epitope distinct from the binding site of the muteins to c-Met by allosteric effects.

An embodiment of the phage display technique (reviewed in Kay, B. K. et al. (1996), supra; Lowman, H. B. (1997) supra or Rodi, D. J., and Makowski, L. (1999), supra) using temperent M13 phage is given as an example of a selection method that can be employed in the present invention. Another embodiment of the phage display technology that can be used for selection of muteins of the invention (see the Experimental Section) is the hyperphage phage technology as described by Broders et al. (Broders et al. (2003) "Hyperphage. Improving antibody presentation in phage display." *Methods Mol. Biol.* 205:295-302). Other temperent phage such as f1 or lytic phage such as T7 may be employed as well. For the exemplary selection method, M13 phagemids are produced which allow the expression of the mutated lipocalin nucleic acid sequence as a fusion protein with a signal sequence at the N-terminus, preferably the OmpA-signal sequence, and with the capsid protein pIII of the phage M13 or fragments thereof capable of being incorporated into the phage capsid at the C-terminus. The C-terminal fragment ΔpIII of the phage capsid protein comprising amino acids 217 to 406 of the wild type sequence is preferably used to produce the fusion proteins. Especially preferred in one embodiment is a C-terminal fragment of pIII, in which the cysteine residue at position 201 is missing or is replaced by another amino acid.

Accordingly, a further embodiment of the methods of the invention involves operably fusing a nucleic acid coding for the plurality of muteins of human tear lipocalin and resulting from mutagenesis at the 3' end with a gene coding for the coat protein pIII of a filamentous bacteriophage of the M13-family or for a fragment of this coat protein, in order to select at least one mutein for the binding of c-Met.

The fusion protein may comprise additional components such as an affinity tag, which allows the immobilization, detection and/or purification of the fusion protein or its parts. Furthermore, a stop codon can be located between the sequence regions encoding the lipocalin or its muteins and the phage capsid gene or fragments thereof, wherein the stop codon, preferably an amber stop codon, is at least partially translated into an amino acid during translation in a suitable suppressor strain.

For example, the phasmid vector pTLPC27, now also called pTlc27 that is described in the International patent application PCT/EP2007/057971 can be used for the preparation of a phagemid library encoding human tear lipocalin muteins. The inventive nucleic acid molecules coding for the tear lipocalin muteins can be inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired. Alternatively, any other suitable phagemid vector, such as, for example, the vector pTLPC59 that is used in the Examples of the present application (see Example 1 and FIG. 1) can also be used for the preparation of the phagemid library. The vector pTLPC59 is identical to the vector pTLc27 with the exception that the library gene contract for phage display is placed under the control of a lac p/o instead of a tet p/o and is genetically fused to the full length gene III of VCSM13 phage.

The resulting library can be subsequently superinfected in liquid culture with an appropriate M13-helper phage or hyperphage in order to produce functional phagemids. The recombinant phagemid displays the lipocalin mutein on its surface as a fusion with the coat protein pIII or a fragment thereof, while the N-terminal signal sequence of the fusion protein is normally cleaved off. On the other hand, it also bears one or more copies of the native capsid protein pIII supplied by the helper phage and is thus capable of infecting a recipient, in general a bacterial strain carrying an F- or F'-plasmid. In case of hyperphage display, the hyperphagemids display the lipocalin muteins on their surface as a fusion with the infective coat protein pIII but no native capsid protein. During or after infection with helper phage or hyperphage, gene expression of the fusion protein between the lipocalin mutein and the capsid protein pIII can be induced, for example by addition of anhydrotetracycline. The induction conditions are chosen such that a substantial fraction of the phagemids obtained displays at least one lipocalin mutein on their surface. In case of hyperphage display induction conditions result in a population of hyperphagemids carrying between three and five fusion proteins consisting of the lipocalin mutein and the capsid protein pIII. Various methods are known for isolating the phagemids, such as precipitation with polyethylene glycol. Isolation typically occurs after an incubation period of 6-8 hours.

The isolated phasmids can then be subjected to selection by incubation with the desired target (i.e. the extracellular domains of c-Met or portions or fragments thereof), wherein the target is presented in a form allowing at least temporary immobilization of those phagemids which carry muteins with the desired binding activity as fusion proteins in their coat. Among the various embodiments known to the person skilled in the art, the target can, for example, be conjugated with a carrier protein such as serum albumin and be bound via this carrier protein to a protein binding surface, for example polystyrene. Microtiter plates suitable for ELISA techniques or so-called "immuno-sticks" can preferably be used for such an immobilization of the target. Alternatively, conjugates of the target with other binding groups, such as biotin, can be used. The target can then be immobilized on a surface which selectively binds this group, for example microtiter plates or paramagnetic particles coated with streptavidin, neutravidin or avidin. If the target is fused to an Fc portion of an immunoglobulin, immobilization can also be achieved with surfaces, for example microtiter plates or paramagnetic particles, which are coated with protein A or protein G.

Non-specific phagemid-binding sites present on the surfaces can be saturated with blocking solutions as they are known for ELISA methods. The phagemids are then typically brought into contact with the target immobilized on the surface in the presence of a physiological buffer. Unbound phagemids are removed by multiple washings. The phagemid particles remaining on the surface are then eluted. For elution, several methods are possible. For example, the phagemids can be eluted by addition of proteases or in the presence of acids, bases, detergents or chaotropic salts or under moderately denaturing conditions. A preferred method is the elution using buffers of pH 2.2, wherein the eluate is subsequently neutralized. Alternatively, a solution of the free target (i.e. the extracellular domains of c-Met or portions or fragments thereof), can be added in order to compete with the immobilized target for binding to the phagemids or target-specific phagemids can be eluted by competition with immunoglobulins or natural liganding proteins which specifically bind to the target of interest.

Afterwards, E. coli cells are infected with the eluted phagemids. Alternatively, the nucleic acids can be extracted from the eluted phagemids and used for sequence analysis, amplification or transformation of cells in another manner. Starting from the E. coli clones obtained in this way, fresh phagemids or hyperphagemids are again produced by superinfection with M13 helper phages or hyperphage according to the method described above and the phagemids amplified in this way are once again subjected to a selection on the immobilized target. Multiple selection cycles are often necessary in order to obtain the phagemids with the muteins of the invention in sufficiently enriched form. The number of selection cycles is preferably chosen such that in the subsequent functional analysis at least 0.1% of the clones studied produce muteins with detectable affinity for the given target. Depending on the size, i.e. the complexity of the library employed, 2 to 8 cycles are typically required to this end.

For the functional analysis of the selected muteins, an E. coli strain can then be infected with the phagemids obtained from the selection cycles and the corresponding double stranded phasmid DNA is isolated. Starting from this phasmid DNA, or also from the single-stranded DNA extracted from the phagemids, the nucleic acid sequences of the selected muteins of the invention can be determined by the methods known in the art and the amino acid sequence can be deduced therefrom. The mutated region or the sequence of the entire tear lipocalin mutein can be subcloned on another expression vector and expressed in a suitable host organism. For example, the vector pTlc26 described in International Patent Application PCT/EP2007/057971 can be used for expression in E. coli strains such as E. coli TG1. The muteins of tear lipocalin thus produced can be purified by various biochemical methods. The tear lipocalin muteins produced, for example with pTlc26, carry the affinity peptide Strep-Tag® II (Schmidt et al., supra) at their C-termini and can therefore preferably be purified by streptavidin affinity chromatography.

The selection can also be carried out by means of other methods. Many corresponding embodiments are known to the person skilled in the art or are described in the literature. Moreover, a combination of methods can be applied. For example, clones selected or at least enriched by "phage display" can additionally be subjected to "colony screening". This procedure has the advantage that individual clones can directly be isolated with respect to the production of a tear lipocalin mutein with detectable binding affinity for c-Met or, for example an extracellar domain of c-Met.

In addition to the use of E. coli as host organism in the "phage display" technique or the "colony screening" method, other bacterial strains, yeast or also insect cells or mammalian cells can be used for this purpose. Further to the selection of a tear lipocalin mutein from a random (naïve) library as described above, evolutive methods including limited mutagenesis can also be applied in order to optimize a mutein that already possesses some binding activity for the target with respect to affinity or specificity for the target after repeated screening cycles.

Once a mutein with affinity to c-Met or a domain or a fragment thereof has been selected, it is additionally possible to subject such a mutein to another mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation", can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) J. Mol. Biol. 255, 589-603. Other methods of random mutagenesis that are suitable for such purposes include random insertion/deletion (RID) mutagenesis as described by Murakami, H et al. (2002) Nat. Biotechnol. 20, 76-81 or non homologous random recombination (NRR) as described by Bittker, J. A et al. (2002) Nat. Biotechnol. 20, 1024-1029. If desired, affinity maturation can also be carried out according to the procedure described in WO 00/75308 or Schlehuber, S. et al., (2000) J. Mol. Biol. 297, 1105-1120, where muteins of the bilin-binding protein having high affinity to digoxigenin were obtained. A further approach for improving the affinity is to carry out positional saturation mutagenesis. In this approach "small" nucleic acid libraries can be created in which amino acid exchanges/mutations are only introduced at single positions within any of the four loop segments defined here (cf., Example 21). These libraries are then directly subjected to a selection step (affinity screening) without further rounds of panning. This approach allows the identification of residues that contribute to improved binding of the desired target and allows identification of "hot spots" that are important for the binding. With such an approach the identification of key residues within the first two segments (sequence positions 24-36 or 56-58) is possible, for example.

In a further aspect, the present invention is directed to a mutein of human tear lipocalin having detectable binding affinity to c-Met or a domain or portion thereof, which is obtainable by or obtained by the above-detailed methods of the invention.

In one embodiment, the mutein of human tear lipocalin obtained according to the above methods includes the substitution of at least one or of both of the cysteine residues occurring at each of the sequences positions 61 and 153 by another amino acid and the mutation of at least one amino acid residue at any one of the sequence positions 26-34, 56-58, 80, 83, 104-106, and 108 of the linear polypeptide sequence of mature human tear lipocalin. The positions 24-36 are comprised in the AB loop, the positions 53-66 are comprised in the CD loop, the positions 69-77 are comprised in the EF loop and the positions 103-110 are comprised in the GH loop in the binding site at the open end of the β-barrel structure of tear lipocalin. The definition of these four loops is used herein in accordance with Flower (Flower, D. R. (1996), supra and Flower, D. R. et al. (2000), supra). Usually, such a mutein comprises at least 2, 3, 4, 5, 6, 8, 10, 12, 14, 15, 16, 17 or 18 mutated amino acid residues at the sequence positions 26-34, 56-58, 80, 83, 104-106, and 108 of the linear polypeptide sequence of mature human tear lipocalin. In a specific embodiment, the mutein comprises the amino acid substitutions Cys 61→Ala, Phe, Lys, Arg, Thr, Asn, Tyr, Met, Ser, Pro or Trp and Cys 153→Ser or Ala. Such a substitution has proven useful to prevent the formation of the naturally occurring disulphide bridge linking Cys 61 and Cys 153, and thus to facilitate handling of the mutein.

In still another embodiment, the mutein comprises at least one additional amino acid substitution selected from Arg 111→Pro and Lys 114→Trp. A mutein of the invention may further comprise the cysteine at position 101 of the sequence of native mature human tear lipocalin substituted by another amino acid. This substitution may, for example, be the mutation Cys 101→Ser or Cys 101→Thr.

The lipocalin muteins of the invention may comprise the wild type (natural) amino acid sequence outside the mutated amino acid sequence positions. On the other hand, the lipocalin muteins disclosed herein may also contain amino acid mutations outside the sequence positions subjected to mutagenesis as long as those mutations do not interfere with the binding activity and the folding of the mutein. Such mutations can be accomplished very easily on DNA level using established standard methods (Sambrook, J. et al. (1989) *Molecular Cloning: A Laboratory Manual,* 2nd Ed., Cold Spring Harbor Laboratory Press, Cold Spring Harbor, N.Y.). Possible alterations of the amino acid sequence are insertions or deletions as well as amino acid substitutions. Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence. In addition, instead of replacing single amino acid residues, it is also possible to either insert or delete one or more continuous amino acids of the primary structure of tear lipocalin as long as these deletions or insertion result in a stable folded/functional mutein (see for example, the experimental section in which muteins with truncated N- and C-terminus are generated).

Such modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. However, it is also possible to deliberately mutate other amino acid sequence position to cysteine in order to introduce new reactive gaups, for example for the conjugation to other compounds, such as polyethylene glycol (PEG), hydroxyethyl starch (HES), biotin, peptides or proteins, or for the formation of non-naturally occurring disulphide linkages. Exemplary possibilities of such a mutation to introduce a cysteine residue into the amino acid sequence of a human tear lipocalin mutein include the substitutions Thr 40→Cys, Glu 73→Cys, Arg 90→Cys, Asp 95→Cys, Lys 121→Cys, Asn 123→Cys and Glu 131→Cys. The generated thiol moiety at the side of any of the amino acid positions 40, 73, 90, 95, 121, 123 and/or 131 may be used to PEGylate or HESylate the mutein, for example, in order to increase the serum half-life of a respective tear lipocalin mutein. The mutein S244.2-H08 into which a cysteine is introduced at any these sequence positions (see Example 9) is an illustrative example of such muteins of the invention. The side chain of any of the cystein residues can of course be used not only for conjugation of serum half-life increasing compounds but as well for conjugation of any wanted conjugation partner such as an organic molecule, an enzyme label, a toxin, a cystostatic agent, a pharmaceutically suitable radioactive label, a fluorescent label, a chromogenic label, a luminescent label, a hapten, digoxigenin, biotin, a metal complexe, a metal or colloidal gold, to name only a few evocative examples. The conjugation can be carried out using any convential coupling method known in the art (see for instance Example 18, in which the cystein residue can be activated by a reagent such as Tris[2-carboxyethyl]phosphine (TCEP) or dithiotreitol (DTT) and then further reacted with a reagent such as 3-N-maleimido-6-hydraziniumpyridine hydrochloride (HYNIC).

The present invention also encompasses truncated muteins (i.e. fragments) as defined above, in which for example, the first four N-terminal amino acid residues of the sequence of mature human tear lipocalin (His-His-Leu-Leu (SEQ ID NO: 53); positions 1-4) and/or the last two C-terminal amino acid residues (Ser-Asp; positions 157-158) of the sequence of mature human tear lipocalin have been deleted (cf. also the Examples and the attached Sequence Listings).

The lipocalin muteins of the invention are able to bind the desired target, i.e. c-Met receptor tyrosin kinase or a domain or fragment thereof with detectable affinity, i.e. with a dissociation constant of at least 200 nM. Presently preferred in some embodiments are lipocalin muteins, which bind the desired target with a dissociation constant for a given target of at least 100, 20, 1 nM or even less. The binding affinity of a mutein to the desired target can be measured by a multitude of methods such as fluorescence titration, competition ELISA or surface plasmon resonance (BIAcore).

It is readily apparent to the skilled person that complex formation is dependent on many factors such as concentration of the binding partners, the presence of competitors, ionic strength of the buffer system etc. Selection and enrichment is generally performed under conditions allowing the isolation of lipocalin muteins having, in complex with the desired target (c-Met or a domain or fragment thereof), a dissociation constant of at least 200 nM. However, the washing and elution steps can be carried out under varying stringency. A selection with respect to the kinetic characteristics is possible as well. For example, the selection can be performed under conditions, which favor complex formation of the target with muteins that show a slow dissociation from the target, or in other words a low $k_{off}$ rate. Alternatively, selection can be performed under conditions, which favour fast formation of the complex between the mutein and the target, or in other words a high $k_{on}$ rate. As a further illustrative alternative, the screening can be performed under conditions that select for improved thermostability of the muteins (compared to either wild type tear lipocalin or a mutein that already has affinity towards a pre-selected target) or for a pH stability of the mutein.

A tear lipocalin mutein of the invention typically exists as monomeric protein. However, it is also possible that an inventive lipocalin mutein is able to spontaneously dimerise or form higher oligomers. Although the use of lipocalin muteins that form stable monomers may be preferred for some applications, e.g. because of faster diffusion and better tissue penetration, the use of lipocalin muteins that spontaneously form stable homodimers or multimers may be advantageous in other instances, since such multimers can provide for a (further) increased affinity and/or avidity to a given target. Furthermore, oligomeric forms of the lipocalin mutein may have slower dissociation rates or prolonged serum half-life. If dimerisation or multimerization of muteins that form stable monomers is desired, this can for example be achieved by fusing respective oligomerization domains such as jun-fos domains or leucin-zippers to muteins of the invention or by the use of "Duocalins" (see also below).

A tear lipocalin mutein of the invention may be used for complex formation with c-Met or a domain or fragment thereof, for example, in vitro, for ex vivo diagnostic purposes or in vivo, for therapeutic purposes.

In general, the term "fragment", as used herein with respect to c-Met, relates to N-terminally and/or C-terminally shortened protein or peptide ligands, which retain the capability of the full length ligand to be recognized and/or bound by a mutein according to the invention. The term "domain" in relation to c-Met is to be understood in accordance with the regular meaning used in the art. For example, the term "domain" comprise the sema domains as structurally defined by Stamos et al., The EMBO Journal, Vol. 23, pages 2325-2335, 2004 (see for example, FIG. 3a or FIG. 4 of Stamos et al.), the PSI domain, the IgG-like domains, the transmembrane domain or also the tyrosine kinase domain as structurally defined by Schiering et al., Proc. Natl. Acad. Sci USA, Vol. 100, No. 22, pahes 12654-12659, 2003). The term "domain" also comprises the entire extracellular portion of c-Met formed by residues Met1 to Thr 932 of the full length receptor protein or truncated fragments formed, for example, by residues 2, 3, 4, 5, 6 to residues 920, 925, 930 or 931 of the full length receptor. As mentioned above, by use of for example, the entire extracellular domains or only some of the extracellular domains, for example, the sema domains, it is possible to generate either muteins that bind to the HGF binding site (and then possibly have an antagonist binding mode with respect to HGF) or also muteins that have a non-antagonist binding mode in relation to HGF binding.

In this context it is also noted that the complex formation between the respective mutein and c-Met or a domain or fragment thereof is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective mutein and its ligand) given here may vary within a certain experimental range, depending on the method and experimental setup that is used for determining the affinity of a particular lipocalin mutein for a given ligand. This means, there may be a slight deviation in the measured $K_D$ values or a tolerance range depending, for example, on whether the $K_D$ value was determined by surface plasmon resonance (Biacore) or by competition ELISA.

In a specific embodiment of the invention a tear lipcalin mutein comprises with respect to the amino acid sequence of mature human tear lipocalin at least 6, 8, 10, 12, 14, 16 or 17 amino acid substitutions with respect to the amino acid sequence of mature human tear lipocalin, which are selected from the group consisting of Arg 26→Thr, Val, Pro, Ser, Gly; Glu 27→Gln, Gly, Val, Ser; Phe 28→Met, Asp, Pro 29→Leu, Ile, Ala, Trp; Glu 30→Leu, Gly, Arg, Phe; Met 31→Ser; Asn 32→Leu, Arg, Val, Gln; Leu 33→Tyr, Val, Ile, Thr, Phe; Glu 34→Val, Arg, Ala; Leu 56→Asn; Ile 57→Gln; Ser 58→Ile, Val; Asp 80→Tyr; Lys 83→Ala; Glu 104→Asp; Leu 105→Thr; His 106→Trp; and Lys 108→Gly SEQ ID NO: 56).

In one more specific embodiment, a mutein of the invention further comprising at least one amino acid substitution selected from the group consisting of Thr 37→Ser; Met 39→Ile, Leu; Asn 48→Ser; Lys 52→Thr, Met; Met 55→Leu; Lys 65→Arg, Leu; Ala 79→Leu, Ser; Ala 86→Thr; and Ile 89→Ser, Gln, Thr, His (SEQ ID NO: 58).

In another more specific embodiment a mutein comprises the amino acid substitutions: Arg 26→Thr; Glu 27→Gln; Glu 30→Leu; Met 31→Ser; Asn 32→Leu; Leu 33→Tyr; Glu 34→Val; Leu 56→Asn; Ile 57→Gln; Asp 80→Tyr; Lys 83→Ala; Glu 104→Asp; Leu 105→Thr; His 106→Trp; and Lys 108→Gly (SEQ ID NO: 59).

In still another more specific embodiment of the invention, a mutein of the invention comprises the amino acid substitutions: Met 31→Ser; Leu 56→Asn; Ile 57→Gln; Asp 80→Tyr; Lys 83→Ala; Glu 104→Asp; Leu 105→Thr; His 106→Trp; and Lys 108→Gly (SEQ ID NO: 60).

In other embodiments, a mutein of the invention may comprise one of the following sets of amino acid substitutions:

(1) Arg 26→Thr; Glu 27→Gln; Phe 28→Met; Glu 30→Leu; Met 31→Ser; Asn 32→Leu; Leu 33→Tyr; Glu 34→Val; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly (SEQ ID NO: 62);

(2) Arg 26→Thr; Glu 27→Gln; Phe 28→Asp; Glu 30→Leu; Met 31→Ser; Asn 32→Leu; Leu 33→Tyr; Glu 34→Val; Leu 56→Asn; Ile 57→Gln; Ser 58→Val; Asp 80 Tyr; Lys 83→Ala; Glu 104→Asp; Leu 105→Thr; His 106→Trp; and Lys 108→Gly SEQ ID NO: 63);

(3) Arg 26→Thr; Glu 27→Gln; Phe 28→Asp; Glu 30→Leu; Met 31→Ser; Asn 32→Leu; Leu 33→Tyr; Glu 34→Val; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly (SEQ ID NO: 64);

(4) Arg 26→Val; Glu 27→Gly; Phe 28→Asp; Pro 29→Leu; Glu 30→Gly; Met 31→Ser; Asn 32→Arg; Leu 33→Val; Glu 34→Val; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly (SEQ ID NO: 65);

(5) Arg 26→Pro; Glu 27→Gly; Phe 28→Asp; Pro 29→Ile; Glu 30→Arg; Met 31→Ser; Asn 32→Leu; Leu 33→Ile; Glu 34→Val; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly (SEQ ID NO: 66);

(6) Arg 26→Ser; Phe 28→Asp; Pro 29→Ala; Glu 30→Phe; Met 31→Ser; Asn 32→Val; Leu 33→Thr; Glu 34→Val; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly SEQ ID NO: 67);

(7) Arg 26→Val; Glu 27→Val; Phe 28→Asp; Pro 29→Trp; Glu 30→Arg; Met 31→Ser; Asn 32→Gln; Leu 33→Val; Glu 34→Arg; Leu 56→Asn; Ile 57→Gln; Ser 58 Ile; Asp 80→Tyr; Lys 83→Ala; Glu 104→Asp; Leu 105→Thr; His 106→Trp; and Lys 108→Gly (SEQ ID NO: 68); and (8) Arg 26→Gly; Glu 27→Ser; Phe 28→Asp; Pro 29→Trp; Met 31→Ser; Asn 32→Val; Leu 33→Phe; Glu 34→Ala; Leu 56→Asn; Ile 57→Gln; Ser 58→Ile; Asp 80→Tyr; Lys 83 Ala; Glu 104→Asp; Leu 105→Thr; His 106→Trp; and Lys 108→Gly SEQ ID NO: 69).

The human tear lipocalin mutein binding c-Met or a domain or fragment thereof may comprise, consists essentially of or consist of any one of the amino acid sequences set forth in any one of SEQ ID No.: 1, SEQ ID NO: 4-9, SEQ ID NO: 22-26, or SEQ ID NO: 32-35 and 37-49 or of a fragment or variant thereof. In one embodiment, the mutein according to the invention comprises, consists essentially of or consists of the amino acid sequence set forth in SEQ ID NO: 1, 4, 5, 6, 7, 8, 9, 22 to 26, 32 to 35, or 42 to 49 or a fragment or variant thereof. In this regard, it is noted that all of the muteins disclosed herein can be linked, either N- or C-terminal to a affinity tag such as pentahistidine tag (SEQ ID NO: 54), a hexahistidine tag (SEQ ID NO: 55) or a Streptag® (cf. SEQ ID Nos: 37 to 41, for example, in which a hexahistidine tag (SEQ ID NO: 55) is fused to the C-terminus of the muteins). Thus, the present application encompasses also all explicitly and generic described muteins equipped with such tags.

The term "fragment" as used in the present invention in connection with the muteins of the invention relates to proteins or peptides derived from full-length mature human tear lipocalin that are N-terminally and/or C-terminally shortened, i.e. lacking at least one of the N-terminal and/or C-terminal amino acids. Such fragments comprise preferably at least 10, more preferably 20, most preferably 30 or more consecutive amino acids of the primary sequence of mature human tear lipocalin and are usually detectable in an immunoassay of mature human tear lipocalin.

The term "variant" as used in the present invention relates to derivatives of a protein or peptide that comprise modifications of the amino acid sequence, for example by substitution, deletion, insertion or chemical modification. Preferably, such modifications do not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

In this context, it is noted that the muteins of the invention have been found to be stable within a large pH range from about pH 2.5 to about pH 9.5, for example, within a pH in the range of about pH 3.0 to about pH 9.2.

Also included in the scope of the present invention are the above muteins, which have been altered with respect to their potential immunogenicity.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. In order to reduce immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class I molecules (Altuvia et al. (1995) *J. Mol. Biol.* 249: 244-250).

Such an approach may also be utilized to identify potential T-cell epitopes in the muteins of the invention and to make depending on its intended use a selection of a specific mutein on the basis of its predicted immunogenicity. It may be furthermore possible to subject peptide regions which have been predicted to contain T-cell epitopes to additional mutagenesis to reduce or eliminate these T-cell epitopes and thus minimize immunogenicity. The removal of amphipathic epitopes from genetically engineered antibodies has been described (Mateo et al. (2000) *Hybridoma* 19(6):463-471) and may be adapted to the muteins of the present invention. The muteins thus obtained may possess a minimized immunogenicity, which is desirable for their use in therapeutic and diagnostic applications, such as those described below.

For some applications, it is also useful to employ the muteins of the invention in a conjugated form. Accordingly, the invention is also directed to lipocalin muteins which are conjugated to a conjungation partner that may be selected from the group consisting of an enzyme label, a colored label, a cytostatic agent, a label that can be photoactivated and which is suitable for use in photodynamic therapy, haptens, digoxigenin, biotin, a chermatherapeutic metal, or a chemotherapeutic metal, and colloidal gold. The mutein may also be conjugated to an organic drug molecule. The term "organic molecule" as used herein preferably denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

In general, it is possible to label a tear lipocalin mutein described herein with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation. Alkaline phosphatase, horseradish peroxidase or β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the present invention. The muteins of the invention may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). Examples of suitable toxins include, but are not limited to pertussis-toxin, diphtheria toxin, ricin, saporin, pseudomonas exotoxin, calicheamicin or a derivative thereof, a taxoid, a maytansinoid, a tubulysin or a dolastatin analogue. The dolastatin analogue may be auristatin E, monomethylauristatin E, auristatin PYE and auristatin PHE. Examples of cytostatic agent include, but are not limited to Cisplatin, Carboplatin, Oxaliplatin, 5-Fluorouracil, Taxotere (Docetaxel), Paclitaxel, Anthracycline (Doxorubicin), Methotrexate, Vinblastin, Vincristine, Vindesine, Vinorelbine, Dacarbazine, Cyclophosphamide, Etoposide, Adriamycine, Camptotecine, Combretatastin A-4 related compounds, sulfonamides, oxadiazolines, benzo[b]thiophenessynthetic spiroketal pyrans, monotetrahydrofuran compounds, curacin and curacin derivatives, methoxyestradiol derivatives and Leucovorin. The lipocalin muteins of the invention may also be conjugated with therapeutically active nucleic acids such as antisense nucleic acid molecules, small interfering RNAs, micro RNAs or ribozymes. Such conjugates can be produced by methods well known in the art.

In one embodiment, the muteins of the invention may also be coupled to a targeting moiety that targets a specific body region in order to deliver the inventive muteins to a desired region or area within the body. One example wherein such modification may be desirable is the crossing of the blood-brain-barrier. In order to cross the blood-brain barrier, the muteins of the invention may be coupled to moieties that facilitate the active transport across this barrier (see Gaillard P J, e al., Diphtheria-toxin receptor-targeted brain drug delivery. *International Congress Series*, 2005 1277:185-198 or Gaillard P J, e al. Targeted delivery across the blood-brain barrier. *Expert Opin Drug Deliv.* 2005 2(2): 299-309. Such moieties are for example available under the trade name 2B-Trans™ (to-BBB technologies B V, Leiden, N L).

As indicated above, a mutein of the invention may in some embodiments be conjugated to a moiety that extends the serum half-life of the mutein (in this regard see also International Patent Application PCT/EP2007/057971 or also PCT publication WO 2006/56464 where such conjugation strategies are described with references to muteins of human neutrophile gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, *Pharmacol. Rev.* 52, 1-9), an Fc part of an immunoglobulin, a CH3 domain of an immunoglobulin, a CH4 domain of an immunoglobulin, albumin or a fragment thereof, an albumin binding peptide, an albumin binding protein, an IgG-Fc-binding protein, or a transferrin to name only a few. The albumin binding protein may be a bacterial albumin binding protein, an antibody, an antibody fragment including domain antibodies (see U.S. Pat. No, 6,696,245, for example), a lipocalin mutein or another protein or protein domain with binding activity for albumin. Accordingly, suitable conjugation partners for extending the half-life of a lipocalin mutein of the invention include albumin (Osborn, B. L. et al. (2002) Pharmacokinetic and pharmacodynamic studies of a human serum albumin-interferon-alpha fusion protein in cynomolgus monkeys *J. Pharmacol. Exp. Ther.* 303, 540-548), or an albumin binding protein, for example, a bacterial albumin binding domain, such as the one of streptococcal protein G (König, T. and Skerra, A. (1998) Use of an albumin-binding domain for the selective immobilisation of recombinant capture antibody fragments on ELISA plates. *J. Immunol. Methods* 218, 73-83). Other examples of albumin binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis, M. S., Zhang, M., Meng, Y. G., Kadkhodayan, M., Kirchhofer, D., Combs, D. & Damico, L. A. (2002). "Albumin binding as a general strategy for improving the pharmacokinetics of proteins." *J Biol Chem* 277, 35035-35043).

In other embodiments, albumin itself or a biological active fragment of albumin can be used as conjugation partner of a lipocalin mutein of the invention. The term "albumin" comprises all mammal albumins such as human serum albumin or bovine serum albumin or rat albumin. The albumin or fragment thereof can be recombinantly produced as described in U.S. Pat. No. 5,728,553 or European patent applications EP 0 330 451 and EP 0 361 991. Recombinant human albumin (Recombumin®) Novozymes Delta Ltd. (Nottingham, UK) can be conjugated or fused to a lipocalin mutein in order to extend the half-life of the mutein.

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the invention, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA., USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the muteins of the invention, the SynFusion™ technology, commercially available from Syntonix Pharmaceuticals, Inc (MA, USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of a mutein of the invention is to fuse to the N- or C-terminus of a mutein of the invention long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, preferably polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. No. 6,500,930 or 6,620,413, carbohydrate oligo- and polymers such as starch or hydroxyethyl starch (HES) can be conjugated to a mutein of the invention for the purpose of serum half-life extension.

If one of the above moieties is conjugated to the human tear lipocalin mutein of the invention, conjugation to an amino acid side chain can be advantageous. Suitable amino acid side chains may occur naturally in the amino acid sequence of human tear lipocalin or may be introduced by mutagenesis. In case a suitable binding site is introduced via mutagenesis, one possibility is the replacement of an amino acid at the appropriate position by a cysteine residue. In one embodiment, such mutation includes at least one of Thr 40→Cys, Glu 73→Cys, Arg 90→Cys, Asp 95→Cys, Lys 121→Cys, Asn 123→Cys or Glu Cys substitution (SEQ ID NO: 70). The newly created cysteine residue at any of these positions can in the following be utilized to conjugate the mutein to moiety prolonging the serum half-life of the mutein, such as PEG or an activated derivative thereof.

In another embodiment, in order to provide suitable amino acid side chains for conjugating one of the above moieties to the muteins of the invention artificial amino acids may be introduced by mutagenesis. Generally, such artificial amino acids are designed to be more reactive and thus to facilitate the conjugation to the desired moiety. One example of such an artificial amino acid that may be introduced via an artificial tRNA is para-acetyl-phenylalanine.

For several applications of the muteins disclosed herein it may be advantageous to use them in the form of fusion proteins. In some embodiments, the inventive human tear lipocalin mutein is fused at its N-terminus or its C-terminus to a protein, a protein domain or a peptide such as a signal sequence and/or an affinity tag.

For pharmaceutical applications a mutein of the invention may be fused to a fusion partner that extends the in vivo serum half-life of the mutein (see again PCT publication WO 2006/56464 where suitable fusion partner are described with references to muteins of human neutrophile gelatinase-associated lipocalin with binding affinity for CTLA-4). Similar to the conjugates described above, the fusion partner may be an Fc part of an immunoglobulin, a CH3 domain of an immunoglobulin, a CH4 domain of an immunoglubolin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a lipocalin mutein of the invention include albumin (Osborn, B. L. et al. (2002) supra *J. Pharmacol. Exp. Ther.* 303, 540-548), or an albumin binding protein, for example, a bacterial albumin binding domain, such as the one of streptococcal protein G (König, T. and Skerra, A. (1998) supra *J. Immunol. Methods* 218, 73-83). The albumin binding peptides described in Dennis et al, supra (2002) or US patent application 2003/0069395 having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr can also be used as fusion partner. It is also possible to use albumin itself or a biological active fragment of albumin as fusion partner of a lipocalin mutein of the invention. The term "albumin" comprises all mammal albumins such as human serum albumin or bovine serum albumin or rat serum albumin. The recombinant production of albumin or fragments thereof is well known in the art and for example described in U.S. Pat. No. 5,728,553, European patent application EP 0 330 451 or EP 0 361 991.

The fusion partner may confer new characteristics to the inventive lipocalin mutein such as enzymatic activity or binding affinity for other molecules. Examples of suitable fusion proteins are alkaline phosphatase, horseradish peroxidase, gluthation-S-transferase, the albumin-binding domain of protein G, protein A, antibody fragments, oligomerization domains, lipocalin muteins of same or different binding specificity (which results in the formation of "Duocalins", cf. Schlehuber, S., and Skerra, A. (2001), Duocalins, engineered ligand-binding proteins with dual specificity derived from the lipocalin fold *Biol. Chem.* 382, 1335-1342) or toxins.

In particular, it may be possible to fuse a lipocalin mutein of the invention with a separate enzyme active site such that both "components" of the resulting fusion protein together act on a given therapeutic target. The binding domain of the lipocalin mutein attaches to the disease-causing target, allowing the enzyme domain to abolish the biological function of the target.

Affinity tags such as the Strep-Tag® or Strep-Tag® II (Schmidt, T. G. M. et al. (1996) *J. Mol. Biol.* 255, 753-766), the myc-tag, the FLAG-tag, the His6-tag (SEQ ID NO: 55) or the HA-tag or proteins such as glutathione-S-transferase also allow easy detection and/or purification of recombinant proteins are further examples of preferred fusion partners. Finally, proteins with chromogenic or fluorescent properties such as the green fluorescent protein (GFP) or the yellow fluorescent protein (YFP) are suitable fusion partners for a lipocalin mutein of the invention as well.

The term "fusion protein" as used herein also comprises lipocalin muteins according to the invention containing a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences is known in the art. A preferred signal sequence for secretion a polypeptide into the periplasm of *E. coli* is the OmpA-signal sequence.

The present invention also relates to nucleic acid molecules (DNA and RNA) comprising nucleotide sequences coding for muteins as described herein. Since the degeneracy of the genetic code permits substitutions of certain codons by other codons specifying the same amino acid, the invention is not limited to a specific nucleic acid molecule encoding a mutein of the invention but includes all nucleic acid molecules comprising nucleotide sequences encoding a functional mutein.

Therefore, the present invention also includes a nucleic acid sequence encoding a mutein according to the invention comprising a mutation at at least one codon of any of the amino acid sequence positions 26-34, 56-58, 80, 83, 104-106 and 108 of the linear polypeptide sequence of native mature human tear lipocalin, wherein the codons encoding at least one of the cysteine residues at sequence positions 61 and 153 of the linear polypeptide sequence of the mature human tear lipocalin have been mutated to encode any other amino acid residue.

The invention as disclosed herein also includes nucleic acid molecules encoding tear lipocalin muteins, which comprise additional mutations outside the indicated sequence positions of experimental mutagenesis. Such mutations are often tolerated or can even prove to be advantageous, for example if they contribute to an improved folding efficiency, serum stability, thermal stability or ligand binding affinity of the mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, preferably a promoter sequence. In another preferred embodiment, a nucleic acid molecule of the invention comprises a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the invention can also be part of a vector or any other kind of cloning vehicle, such as a plasmid, a phagemid, a phage, a baculovirus, a cosmid or an artificial chromosome.

In one embodiment, the nucleic acid molecule is comprised in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (reviewed, e.g., in Kay, B. K. et al. (1996) *Phage Display of Peptides and Proteins—A Laboratory Manual*, 1st Ed., Academic Press, New York N.Y.; Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a lipocalin mutein of the invention, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding lipocalin muteins of the invention, and in particular a cloning vector containing the coding sequence of such a lipocalin mutein can be transformed into a host cell capable of expressing the gene. Transformation can be performed using standard techniques (Sambrook, J. et al. (1989), supra). Thus, the invention is also directed to a host cell containing a nucleic acid molecule as disclosed herein.

The transformed host cells are cultured under conditions suitable for expression of the nucleotide sequence encoding a fusion protein of the invention. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g. HeLa cells or CHO cells) or primary mammalian cells The invention also relates to a method for the production of a mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then isolated from this host organism or its culture. It is also possible to produce a protein in vitro, for example by use of an in vitro translation system.

When producing the mutein in vivo a nucleic acid encoding a mutein of the invention is introduced into a suitable bacterial or eukaryotic host organism by means of recombinant DNA technology (as already outlined above). For this purpose, the host cell is first transformed with a cloning vector comprising a nucleic acid molecule encoding a mutein of the invention using established standard methods (Sambrook, J. et al. (1989), supra). The host cell is then cultured under conditions, which allow expression of the heterologous DNA and thus the synthesis of the corresponding polypeptide. Subsequently, the polypeptide is recovered either from the cell or from the cultivation medium.

In some tear lipocalin muteins of the invention, the naturally occurring disulfide bond between Cys 61 and Cys 153 is removed. Accordingly, such muteins (or any other tear lipocalin mutein that does not comprise an intramolecular disulfide bond) can be produced in a cell compartment having a reducing redox milieu, for example, in the cytoplasma of Gram-negative bacteria. In case a lipocalin mutein of the invention comprises intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds. It is, however, also possible to produce a mutein of the invention in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, Seifert C, Hunte C. (2002) "High level production of functional antibody Fab fragments in an oxidizing bacterial cytoplasm." *J. Mol. Biol.* 315, 1-8.).

However, a mutein of the invention may not necessarily be generated or produced only by use of genetic engineering. Rather, a lipocalin mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (reviewed, e.g., in Lloyd-Williams, P. et al. (1997) *Chemical Approaches to the Synthesis of Peptides and Proteins*. CRC Press, Boca Raton, Fields, G. B., and Colowick, S. P. (1997)

*Solid-Phase Peptide Synthesis.* Academic Press, San Diego, or Bruckdorfer, T. et al. (2004) *Curr. Pharm. Biotechnol.* 5, 29-43).

In another embodiment, the muteins of the invention may be produced by in vitro transcription/translation employing well-established methods known to those skilled in the art.

The invention also relates to a pharmaceutical composition comprising at least one inventive mutein of human tear lipocalin or a fusion protein or conjugate thereof and a pharmaceutically acceptable excipient.

The lipocalin muteins according to the invention can be administered via any parenteral or non-parenteral (enteral) route that is therapeutically effective for proteinaceous drugs. Parenteral application methods comprise, for example, intracutaneous, subcutaneous, intramuscular, intratracheal, intranasal, intravitreal or intravenous injection and infusion techniques, e.g. in the form of injection solutions, infusion solutions or tinctures, as well as aerosol installation and inhalation, e.g. in the form of aerosol mixtures, sprays or powders. An overview about pulmonary drag delivery, i.e. either via inhalation of aerosols (which can also be used in intranasal administration) or intracheal instiallation is given by J. S. Patton et al. The lungs as a portal of entry for systemic drug delivery. Proc. Amer. Thoracic Soc. 2004 Vol. 1 pages 338-344, for example). Non-parenteral delivery modes are, for instance, orally, e.g. in the form of pills, tablets, capsules, solutions or suspensions, or rectally, e.g. in the form of suppositories. The muteins of the invention can be administered systemically or topically in formulations containing conventional non-toxic pharmaceutically acceptable excipients or carriers, additives and vehicles as desired.

In one embodiment of the present invention the pharmaceutical is administered parenterally to a mammal, and in particular to humans. Corresponding administration methods include, but are not limited to, for example, intracutaneous, subcutaneous, intramuscular, intratracheal or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan V M and Michniak B B 2004 Am. J. Ther. 11(4): 312-316, can also be used for transdermal delivery of the muteins described herein. Non-parenteral delivery modes are, for instance, oral, e.g. in the form of pills, tablets, capsules, solutions or suspensions, or rectal administration, e.g. in the form of suppositories. The muteins of the invention can be administered systemically or topically in formulations containing a variety of conventional non-toxic pharmaceutically acceptable excipients or carriers, additives, and vehicles.

The dosage of the mutein applied may vary within wide limits to achieve the desired preventive effect or therapeutic response. It will, for instance, depend on the affinity of the compound for a chosen ligand as well as on the half-life of the complex between the mutein and the ligand in vivo. Further, the optimal dosage will depend on the biodistribution of the mutein or its fusion protein or its conjugate, the mode of administration, the severity of the disease/disorder being treated as well as the medical condition of the patient. For example, when used in an ointment for topical applications, a high concentration of the tear lipocalin mutein can be used.

However, if wanted, the mutein may also be given in a sustained release formulation, for example liposomal dispersions or hydrogel-based polymer microspheres, like PolyActive™ or OctoDEX™ (cf. Bos et al., Business Briefing: Pharmatech 2003: 1-6). Other sustained release formulations available are for example PLGA based polymers (PR pharmaceuticals), PLA-PEG based hydrogels (Medincell) and PEA based polymers (Medivas).

Accordingly, the muteins of the present invention can be formulated into compositions using pharmaceutically acceptable ingredients as well as established methods of preparation (Gennaro, A. L. and Gennaro, A. R. (2000) *Remington: The Science and Practice of Pharmacy,* 20th Ed., Lippincott Williams & Wilkins, Philadelphia, Pa.). To prepare the pharmaceutical compositions, pharmaceutically inert inorganic or organic excipients can be used. To prepare e.g. pills, powders, gelatine capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

Another aspect of the present invention relates to a method of treating a disease or disorder in a subject in need thereof. This disease may or may not involve the binding/interaction of the c-Met receptor tyrosin kinase. The disease may be a disease in the development of which the HGF/c-Met pathway is involved. Such a disease or disorder may be a cell proliferative disorder. An example of a cell proliferative disease is cancer. Examples of cancer to be treated include, but are not limited to liver cancer, colon cancer (for example, primary colon cancer, see for instance Clin Cancer Res. 2003, 9(4), pages 1480-1488) colorectal cancer (cf. Zeng et al., Clin. Exp. Metastasis, 200004, 21(5), pages 409-417), hepatocellular carcinoma, papillary renal carcinoma, head and neck squamous cell carcinoma (HNSC), lymph nodes metastases of head and neck squamous carcinoma, for example (see Schiering et al., PNAS, Vol. 100, No. 22, pages 12654-12559, 2003, for example, or the reviews of Trusolino & Comoglio, (2002), Nat. Rev. Cancer, 289-300 or Maulik et al. (2002) *Cytokine Growth Faktor Rev.* 13, 41-59). For such therapeutic purposes tear lipocalin muteins that antagonize the HGF/c-Met pathway and/or toxin fusions or conjugates of a tear lipocalin mutein or conjugates of a tear lipocalin mutein with a cytostatic agent as described above can be used.

The subject in need of such a treatment may be a mammal, such as a human, a dog, a mouse, a rat, a pig, an ape such as cymologous to name only a few illustrative examples.

As is evident from the above disclosure, a mutein of the present invention or a fusion protein or a conjugate thereof can be employed in many applications. In general, such a mutein can be used in all applications antibodies are used, except those with specifically rely on the glycosylation of the Fe part.

Therefore, in another aspect of the invention, the invented muteins of human tear lipocalin can be used for the in vitro detection of given ligand, i.e. c-Met receptor or a domain or fragment thereof. Such use may comprise the steps of contacting the mutein with a sample suspected of containing the given ligand under suitable conditions, thereby allowing formation of a complex between the mutein and the given ligand, and detecting the complexed mutein by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins of human tear lipocalin disclosed herein may also be used for the in vitro separation of a given ligand of human tear lipocalin. Such use may comprise the steps of contacting the mutein with a sample supposed to contain said ligand under suitable conditions, thereby allowing formation of a complex between the mutein and the given ligand, and separating the mutein/ligand complex from the sample.

In both the use of the mutein for the detection of a given ligand as well as the separation of a given ligand, the mutein and/or the target may be immobilized on a suitable solid phase.

The human tear lipocalin muteins of the invention may also be used to target a compound to a preselected site. In one such embodiment, a mutein of human tear lipocalin is used for the targeting of a pharmaceutically active compound to a preselected site in an organism or tissue, comprising of:
a) conjugating the mutein with said compound, and
b) delivering the mutein/compound complex to the preselected site.

The pharmaceutically active compound may be selected from the group consisting of a toxin, a cytostatic agent or a c-Met antagonist. Examples of c-Met antagonists include a monoclonal antibody (which typically binds the extracellular domains of c-Met), or inhibitors that target the intracellular domains (in particular the tyrosine kinase domain). Examples of small molecule inhibitors include, but are not limited to, a 1,3,5, triazine-2,4-diamine derivative as described in WO 2004/031184, a 2-(2-,6-dichlorophenyl-imidazole derivative, a nitrogen containing bicyclic derivative, a 5-benzylsulfonyl and sulfonamide substituted pyrrole indoline (for example, the compound PHA-665752 developed by Sugen and described by Christenson J. G. AACR, Abst 4963 and 6200, 2003, or Sattler M et al, AACR, Abst 1005, 2003).

For such a purpose the mutein is contacted with the c-Met receptor tyro sin kinase or a domain in order to allow complex formation. Then the complex comprising the mutein and the compound of interest are delivered to the preselected site. This use is in particular suitable, but not restricted to, for delivering a drug (selectively) to a preselected site in an organism, such as an infected body part, tissue or organ which is supposed to be treated with the drug. Besides formation of a complex between mutein and compound of interest, the mutein can also be reacted with the given compound to yield a conjugate of mutein and compound. Similar to the above complex, such a conjugate may be suitable to deliver the compound to the preselected target site. Such a conjugate of mutein and compound may also include a linker that covalently links mutein and compound to each other. Optionally, such a linker is stable in the bloodstream but is cleavable in a cellular environment.

The muteins disclosed herein and its derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. For example, muteins of the invention can serve to detect chemical structures by means of established analytical methods (e.g. ELISA or Western Blot) or by microscopy or immunosensorics. Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in in vitro diagnostics and drug delivery, a mutant polypeptide of the invention, which binds, for example, tissue- or tumor-specific cellular surface molecules can be generated.

Figure 1B:
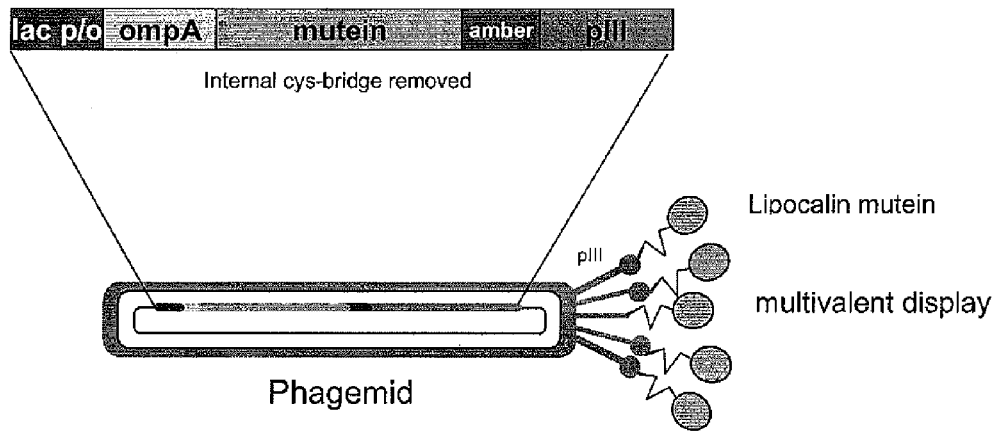
Figure 2:
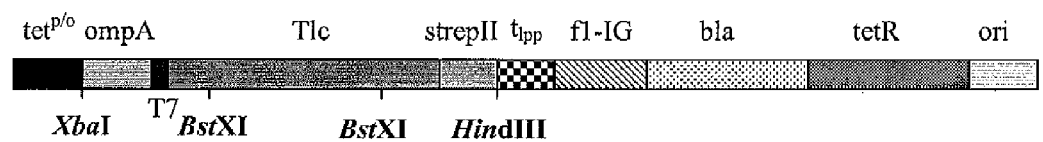
Figure 6:
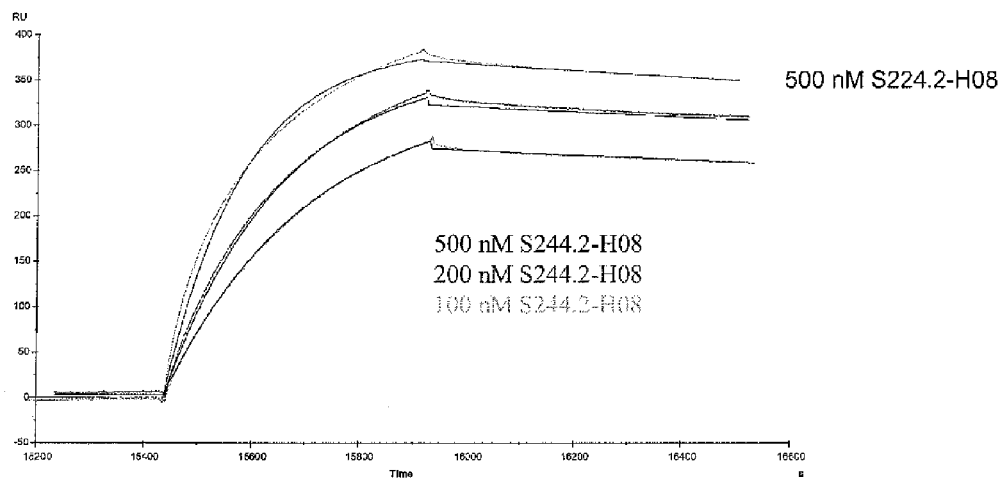
Figure 7:
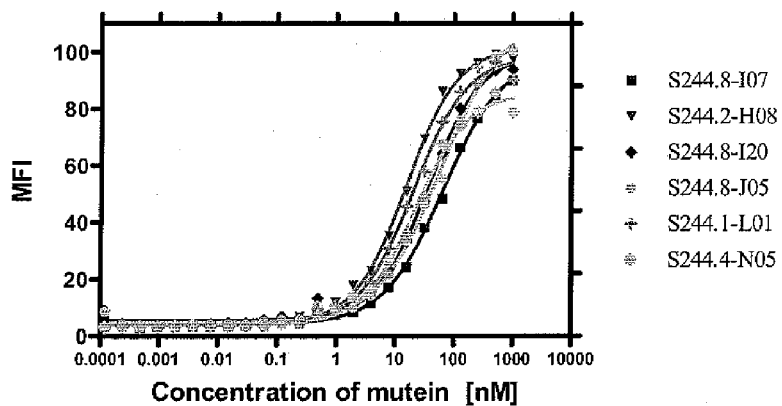
Figure 8:
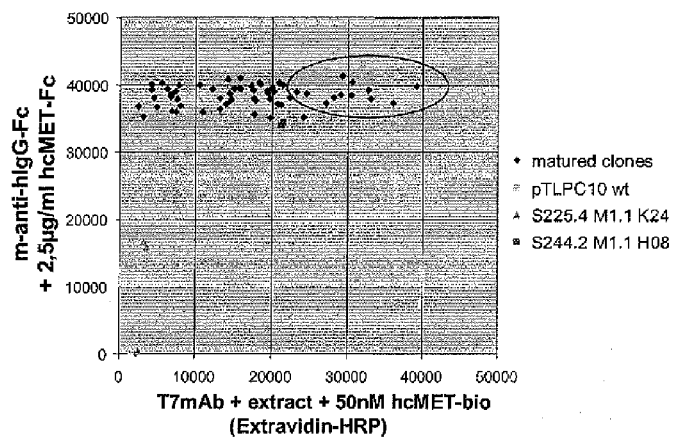

The invention is further illustrated by the following non-limiting Examples and the attached drawings in which:

FIG. 1 shows a map of phasmid vector pTLPC59, with FIG. 1a showing a schematic presentation of the regulatory elements of the vector and FIG. 1b representing a schematic enlargement of the gene construct of the tear lipocalin muteins that is used for expressing the naïve library, FIG. 2 shows a map of the expression vector pTLPC 10, FIG. 3 shows the polypeptide sequences of the tear lipocalin muteins S225.4-K24 (SEQ ID NO: 1) in alignment with the polypeptide sequences of wildtype tear lipocalin (SEQ ID NO: 71), FIG. 4 shows the method of affinity screening via ELISA and the results obtained for muteins with affinity for c-Met, FIG. 5 shows an alignment of the polypeptide sequences of the tear lipocalin muteins S225.4-K24 (residues 20-152 of SEQ ID NO: 1), and S244.2-H08 (residues 20-152 of SEQ ID NO: 4), S244.2-L01 (residues 20-152 of SEQ ID NO: 5), 5244.4-N05 (residues 20-152 of SEQ ID NO: 6), S244.5-J05 (residues 20-152 of SEQ ID NO: 7), S244.8-I20 (residues 20-152 of SEQ ID NO: 8), S244.8-I07 (residues 20-152 of SEQ ID NO: 9), FIG. 6 shows BIAcore measurements of the binding of a human tear lipocalin mutein of the invention (S244.2-H08; SEQ ID NO:4) to c-Met, FIG. 7 shows the result of an affinity assessment of the c-Met binding muteins 5244.2-H08, S244.2-L01, S244.4-N05, S244.5-J05, S244.8-120, S244.8-I07 (SEQ ID NOs.: 4-9) in a cellular context on HT-29 cells, FIG. 8 shows the method of affinity screening via ELISA and the results obtained for muteins with affinity for c-Met, FIG. 9 shows an alignment of the polypeptide sequences of the tear lipocalin muteins S225.4-K24 (residues 1-111 of SEQ ID NO: 1), S244.2-H08 (residues 1-111 of SEQ ID NO: 4), S261.1-L12, S261.1-J01, and S261.1-L17 (residues 1-111 of SEQ ID NOs.: 32-34, respectively). FIG. 9 discloses the "TLc wt" sequence as residues 1-111 of SEQ ID NO: 71.

FIG. 10 shows a map of the expression vector pTLPC 47, "His(6)" disclosed as SEQ ID NO: 55.

Figure 12:
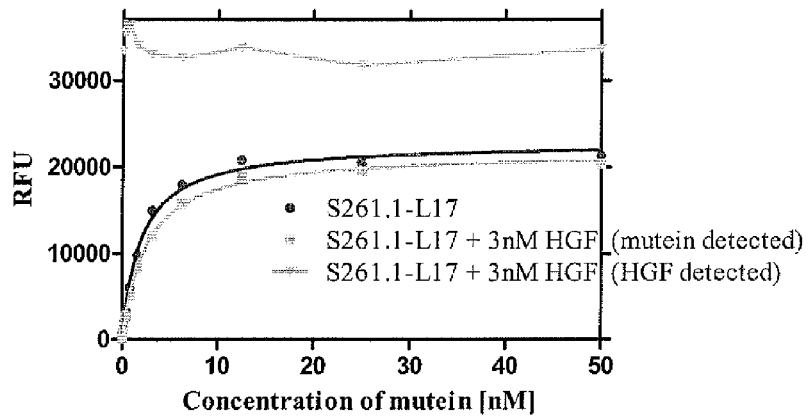
Figure 13:
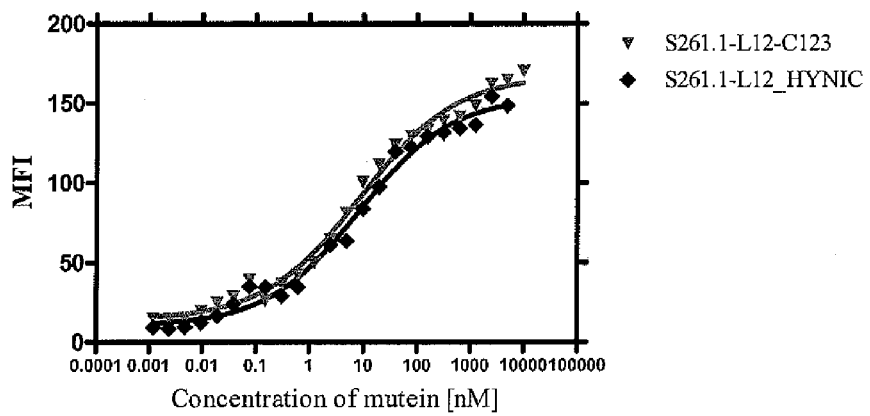
Figure 14:
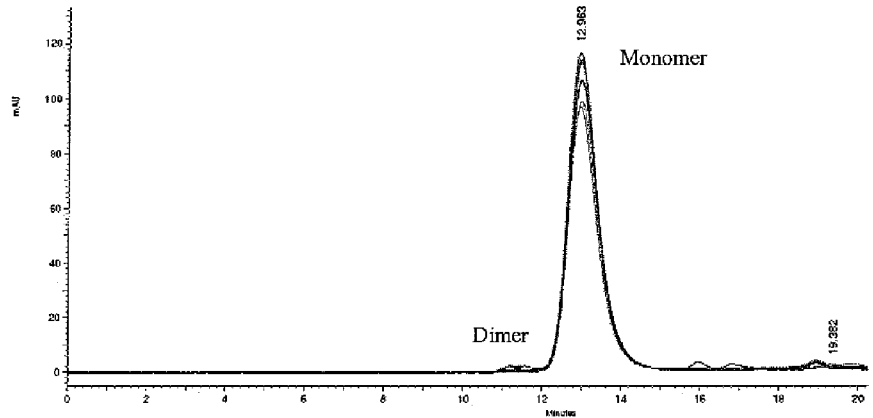
Figures 15, 16:
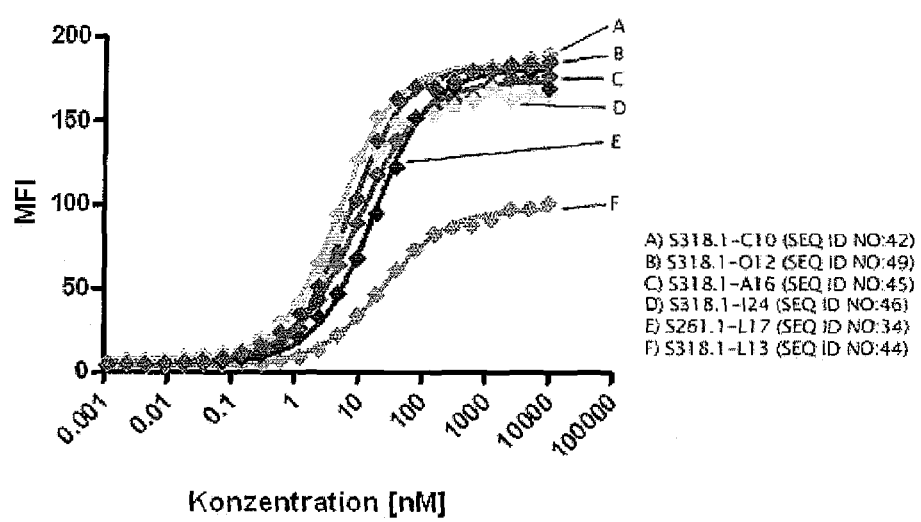

FIG. 11 shows the result of an affinity assessment of the c-Met binding muteins S261.1-L12, S261.1-J01, and S261.1-L17 (SEQ ID NOs.:32-34) in a cellular context on HT-29 cells, FIG. 12 shows competition ELISA measurements of the binding of a human tear lipocalin mutein of the invention (S261.1-L17; SEQ ID NO:34) to c-Met, FIG. 13 shows the result of an affinity assessment of the c-Met binding mutein S261.1-L12_C123 (SEQ ID NO:35) in a cellular context on HT-29 cells, FIG. 14 shows the results of the pH stability test of the tear lipocalin mutein S261.1-J01 (SEQ ID NO:33), FIG. 15 shows an alignment of the polypeptide sequences of further tear lipocalin muteins of the invention (in which further single mutations have been introduced) together with their $K_D$ value for the binding to c-Met, FIG. 16 shows the result of an affinity assessment of the c-Met binding muteins S318.1-C10, S318.1-L13, S318.1-A16, S318.2-I24, and S318.1-012 (SEQ ID NO: 42, 44, 45, 46 and 49) in a cellular context on HT-29 cells.

EXAMPLES

Unless otherwise indicated, established methods of recombinant gene technology were used, for example, as described in Sambrook et al. (supra).

Example 1

Generation of a Library with $1.6 \times 10^{10}$ Independent Tlc Muteins

A random library of tear lipocalin (Tlc) with high complexity was prepared essentially as described in Example 1 of PCT application PCT/EP2007/057971 the disclosure of which is fully incorporated by reference herein with the exception that the library gene construct for phage display pTLPC59 (FIGS. 1a and 1b) is placed under the control of a lac p/o instead of a tet p/o and is genetically fused to the full length gene III of VCSM13 phage.

Tear lipocalin mutein phage production in a multivalent phage display format was realized using M13K07 Hyperphage (Progen) for *E. coli* infection under standard methods as described in literature (M. Kirsch et al. Journal of Immunological Methods 301 (2005) 173-185).

Example 2

Phagemid Presentation and Selection of Tlc Muteins with Affinity for c-Met Receptor Phagemid display and selection was performed employing the phagemids obtained from Example 1 essentially as described in WO 2005/019256 Example 3 with the following modifications: The target protein (c-Met receptor-Fc, R&D systems) was employed at a concentration of 200 nM and was presented to the library as Fc-fusion protein with subsequent capture of the phage-target complex using protein G beads (Dynal). In order to select binders that act non-antagonistic to the natural ligand HGF, an additional wash step was introduced using 200 nM of soluble HGF (R&D systems), before c-Met bound library phages were eluted under basic conditions. Four rounds of selection were performed.

Example 3

Identification of c-Met Receptor-Specific Muteins Using High-Throughput ELISA Screening Screening of the muteins selected according to Example 2 was performed essentially as described in Example 3 of WO 2006/56464. Modifications of the protocol are described in the following: Expression vector was pTLPC10 (FIG. 2). Target protein used was c-Met receptor-Fc (R&D Systems) at 1 μg/ml and 3% milk was used as unrelated control target instead of human serum albumin.

Screening of 2880 clones, selected as described in Example 2, led to the identification of 342 primary hits indicating that successful isolation of muteins from the library had taken place. Using this approach the clone S225.4-K24 (SEQ ID NO: 1) was identified. The sequence of S225.4-K24 is also depicted in FIG. 3.

Example 4

Affinity Maturation of the Mutein S225.4-K24 Using Error-Prone PCR

Generation of a library of variants based on the mutein S225.4-K24 (SEQ ID NO: 1) was performed essentially as described in Example 5 of WO 2006/56464 using the oligonucleotides TL50 bio: TATCTGAAGGCCATGACGGTGGAC (SEQ ID NO: 2) and TL51 bio: TGCCCACGAGCCACACCCCTGGGA (SEQ ID NO: 3) resulting in a library with 5 substitutions per structural gene on average.

Phagemid selection was carried out as described in Example 2 but employing limited target concentration (2 nM, 0.5 nM and 0.1 nM) of c-Met receptor-Fc, and capturing of target and phagemid complex via anti-human IgG-Fc specific mAb immobilized on a polystyrol plate. Additional selections under identical conditions but with combined target limitation (1 nM) and short incubation time (5 minutes) or target limitation (5 nM, 0.5 nM and 0.1 nM) combined with incubation of phagemids at pH 3, 60° C. for 15 min or pH 10, RT, for 30 min were carried out. Four rounds of selection were performed.

Example 5

Affinity Screening of c-Met Receptor-Binding Muteins Using High-Throughput ELISA Screening Screening was performed as described in Example 3 with the modification that concentrations of 2.5 μg/ml or 0.6 μg/ml of c-Met receptor-Fc (R&D Systems) were used. In total 2880 clones were screened resulting in 1510 hits indicating that successful enrichment of matured muteins from the library had taken place. Additionally in an alternative screening setup monoclonal anti-T7 antibody was coated on a polystyrol plate and expressed muteins were captured via T7-tag prior to incubation with limited concentrations of c-Met receptor-Fc (60 nM, 15 nM and 2.5 nM). Binding of c-Met receptor-Fc was detected using a HRP-conjugated polyclonal antibody against the human IgG-Fc domain.

A result from such a screen is depicted in FIG. 4. A large number of muteins selected as described in Example 4 and 5 were identified having improved affinity for c-Met receptor as compared to the mutein S225.4-K24 (SEQ ID NO: 1) which served as the basis for affinity maturation. Using this approach the muteins S244.2-H08, S244.2-L01, S244.4-N05, S244.5-J05, S244.8-I20, S244.8-I07 (SEQ ID NOs.: 4-9) were identified. The sequences of S244.2-H08, S244.2-L01, S244.4-N05, S244.5-J05, S244.8-I20, S244.8-I07 are also depicted in FIG. 5.

Example 6

Production of c-Met Receptor-Binding Muteins

For preparative production of c-Met receptor-specific muteins, *E. coli* K12 strain JM83 harboring the respective mutein encoded on the expression vector pTLPC10 (FIG. 2) was grown in a 2 L shake flask culture in LB-Ampicillin medium according to the protocol described in Schlehuber, S. et al. (*J. Mol. Biol.* (2000), 297, 1105-1120). When larger amounts of protein were needed, the *E. coli* strain W3110 harboring the respective expression vector was used for the periplasmatic production via bench top fermenter cultivation in a 1 l or 10 l vessel based on the protocol described in Schiweck, W., and Skerra, A. *Proteins* (1995) 23, 561-565).

The muteins were purified from the periplasmic fraction in a single step via streptavidin affinity chromatography using a column of appropriate bed volume according to the procedure described by Skerra, A. & Schmidt, T. G. M. (2000) (Use of the Strep-tag and streptavidin for detection and purification of recombinant proteins. *Methods Enzymol.* 326A, 271-304). To achieve higher purity and to remove any aggregated recombinant protein, a gel filtration of the muteins was finally carried out on a Superdex 75 HR 10/30 column (24-ml bed volume, Amersham Pharmacia Biotech) in the presence of PBS buffer. The monomeric protein fractions were pooled, checked for purity by SDS-PAGE, and used for further biochemical characterization.

Example 7

Affinity Measurement Using Surface-Plasmon-Resonance Spectroscopy (SPR)

Affinity measurements were performed essentially as described in Example 9 of WO 2006/56464 with the modifications that approximately 9000 RU of c-Met receptor-Fc (R&D Systems) was directly immobilized on the surface of a CM5 chip (instead of 2000 RU of human CTLA-4 or murine CTLA-4-Fc used as target in WO 2006/56464) and 80 µl of mutein was injected at a concentration of 0.2-0.5 µM (instead of 40 µl sample purified lipocalin muteins at concentrations of 5-0.3 µM as used in WO 2006/56464). The chip surface was regenerated between measurements by injection of 5-10 µl of 50 mM NaOH pH 10, 2.5 M NaCl. The flow rate was held constant at 10 µl/min.

Results from the affinity measurements employing S244.2-H08, S244.2-L01, S244.4-N05, S244.5-J05, S244.8-I20, S244.8-I07 are summarized in Table I and evaluation of sensorgrams exemplary for S244.2-H08 is depicted in FIG. 6.

TABLE I

Affinities of selected muteins of the invention for c-Met receptor as determined by SPR. Mean values are calculated from at least 3 independent measurements.

| Mutein | kon (1/Ms × 10$^4$) | koff (1/s 10$^{-4}$) | KD [nM] |
|---|---|---|---|
| S244.2-H08 | 1.51 | 1.5 | 9.9 |
| S244.2-L01 | 1.24 | 1.96 | 15.8 |
| S244.4-N05 | 1.1 | 2.64 | 24 |
| S244.8-I20 | 0.9 | 2.09 | 23 |
| S244.8-I07 | 0.87 | 4.1 | 47 |
| S244.8-J05 | 0.93 | 1.45 | 15.5 |

Example 8

Affinity Ranking of Lipocalin Muteins on Intact Cells by Flow Cytometry

Lipocalin muteins were titrated on HT-29 cells (ATCC) which show endogenous expression of HGFR/c-Met. Lipocalin muteins were tested in 24 1:2 dilutions starting from 10 µM concentration in a total volume of 30 µl. For each binding reaction, 100,000 cells were incubated in PBS containing 2% Fetal Calf Serum (FCS) for 2 h on at 4° C. Cells were washed twice with PBS, 2% FCS and incubated with 375 ng biotinylated, affinity-purified goat anti tear lipocalin antiserum per reaction for 30 min. After washing, detection was achieved after further 30 min incubation with Streptavidin-Phycoerythrin. Cells were washed and fluorescence was analyzed on a FACS Calibur flow cytometer. Mean Fluorescence Intensity (MFI) was plotted against concentration of the lipocalin mutein and fitted to a sigmoidal dose response curve and EC50 values were determined using GraphPad Prism software.

Titration curves from which EC50 values for S244.2-H08, S244.2-L01, S244.4-N05, S244.5-J05, S244.8-I20, S244.8-I07 were determined are depicted in FIG. 7 and calculated EC50 values are summarized in Table II.

TABLE II

EC50 values and standard deviations of selected muteins of the invention for c-Met receptor as determined by FACS titration on HT-29 cells.

| Clone | EC50 [nM] | STD |
|---|---|---|
| S244.2-H08 | 13.2 | 1.3 |
| S244.2-L01 | 16.8 | 1.7 |
| S244.4-N05 | 18.2 | 18.2 |
| S244.8-I07 | 44.8 | 5.9 |
| S244.8-I20 | 28.1 | 4 |
| S244.8-J05 | 37.8 | 5.5 |

Example 9

Screening of Lipocalin Mutein-Cys Variants

In order to provide a reactive group for site-directed coupling with e.g. activated PEG or a pharmaceutically relevant label, an unpaired cysteine residue was introduced by site-directed mutagenesis. The recombinant mutein carrying the free Cys residue was subsequently produced in *E. coli* as described in Example 6, the expression yield determined and the affinity measured by SPR essentially as described in Example 7.

Cystein was introduced either instead of the amino acids Thr 40, Asp 95, Arg 90, Lys 121, Asn 123 or Val 93 employing pairwise the oligonucleotides

```
H08_T40C forward
                                    (SEQ ID NO: 10)
CGTCTCGGTAACACCCATATGCCTCACGACCCTGGAAGGG
and H08 T40C reverse
                                    (SEQ ID NO: 11)
CCCTTCCAGGGTCGTGAGGCATATGGGTGTTACCGAGACG,
or H08_D95C forward
                                    (SEQ ID NO: 12)
CAGGTCGCACGTGAAGTGCCACTACATCTTTTACTCTGAGGG
and H08_D95C reverse
                                    (SEQ ID NO: 13)
CCCTCAGAGTAAAAGATGTAGTGGCACTTCACGTGCGACCTG,
or
```

-continued

H08_R90C forward
(SEQ ID NO: 14)
CGTGGCATACATCAGCTGCTCGCACGTGAAGGATCAC
and

H08_R90C
(SEQ ID NO): 15
GTGATCCTTCACGTGCGAGCAGCTGATGTATGCCACG,
or

A22_K121C forward
(SEQ ID NO: 16)
GGCAGAGACCCCTGCAACAACCTGGAAGCCTTG
and

A22_K121C reverse
(SEQ ID NO: 17)
CAAGGCTTCCAGGTTGTTGCAGGGGTCTCTGCC,
or

A22_N123C forward
(SEQ ID NO: 18)
GGCAGAGACCCCAAGAACTGCCTGGAAGCCTTGGAG
and

A22_N123C forward
(SEQ ID NO: 19)
CTCCAAGGCTTCCAGGCAGTTCTTGGGGTCTCTGCC,
or

H08_V93C forward
(SEQ ID NO: 20)
CATCAGCAGGTCGCACTGCAAGGATCACTACATCTTTTAC
and

H08_V93C riverse
(SEQ ID NO: 21)
GTAAAAGATGTAGTGATCCTTGCAGTGCGACCTGCTGATG,
respectively.

Exemplary, results from the Cys-screening of the c-Met receptor-specific mutein S244.2-H08 (SEQ ID NO: 4) are given in table III below.

TABLE III

SPR-affinities for c-Met receptor of the mutein S244.2-H08 and mutants thereof comprising amino acid exchanges Thr 40→ Cys (SEQ ID NO: 22), Asn 123→ Cys (SEQ ID NO: 23), Asp 95→ Cys (SEQ ID NO: 24), Arg 90→ Cys (SEQ ID NO: 25), and Lys 121→ Cys (SEQ ID NO: 26).

| Clone | Yield [μg/L] | Affinity [nM] |
|---|---|---|
| S244.2-H08_K121C | 31 | 8 |
| S244.2-H08_N123C | 51 | 14 |
| S244.2-H08_D95C | 15 | 11 |
| S244.2-H08_R90C | 55 | 35 |
| S244.2-H08_T40C | 63 | 40 |
| S244.2-H08_V93C | 31 | 21 |
| S244.2-H08 | 200 | 8 |

Example 10

Affinity Maturation of the Mutein S225.4-K24 Using a Site-Directed Random Approach A library of variants based on the mutein S225.4-K24 (SEQ ID NO: 1) was designed by randomization of the residue positions 28, 39, 52, 5, 58, 65, and 89 to allow for all 20 amino acids on these positions. The library was constructed essentially as described in Example 1 with the modification that three randomized PCR fragments were generated employing pairwise the deoxynucleotides K24_1 GCCAT-GACGGTGGACACGCAGNNSCCGCTGAGCCTCTAC (SEQ NO.: 27) (covering position 28) and K24_2: CAGGGTCGTGAGGGTSNNGGGTGTCACCGAGAC (SEQ NO.: 28) (covering position 39), K24_3: GGGGGCAACCTGGAAGCCNNSGTCAC-CNNSAACCAGNNSGGCCGGTCCCAGGAG GTG, (SEQ NO.: 29) (covering positions 52, 55, and 58) and K24_4: GTATTTTCCCGGCTCATCAGTTTTCTC-CAGGACGGCSNNCACCTCCTGGGACCGGC C (SEQ NO.: 30) (covering position 65), K24_5: GTGCTCACGTG-GCATACATCNNSAGGTCGCACGTGAAGGAC (SEQ NO.: 31) (covering position 89) and TL51bio (SEQ NO.: 3) instead of TL46, TL47, TL48 and TL49, respectively. Phagemid display and selection was performed employing the phagemids essentially as described in Example 2 with the following modifications: The target protein was monomeric c-Met receptor without Fc-portion (R&D systems) in a biotinylated form that allows capturing of target: phagemid complex via neutravidin (Pierce) immobilized on a polystyrol plate. Selection was performed using either limited target concentration (1.5 nM and 0.5 nM and 0.1 nM of biotinylated c-Met receptor) or limited target concentration (3 μg/ml, 1 μg/ml, and 0.3 μg/ml) was combined with shorter incubation time (10 min) or a competitive approach using high excess (10 μM) of purified c-Met specific mutein S244.2-H08 (SEQ Nr.: 4) derived from error prone maturation as described in Example 5. Three rounds of selection were performed.

Example 11

Affinity Screening of c-Met Receptor-Binding Muteins Using High-Throughput ELISA Screening Screening was essentially performed as described in Example 5 in alternative screening setups with the following modifications:
i) monoclonal anti-T7 antibody was coated on a polystyrol plate and expressed muteins were captured via T7-tag prior to incubation with limited concentrations of monomeric c-Met receptor-bio (50 nM, 10 nM and 2.5 nM). Binding of target was detected using a HRP (horseradish peroxidase)-conjugated Extravidin.
ii) Biotinylated c-Met receptor (1 μg/ml) was captured on neutravidin plates. Binding of expressed c-Met specific muteins was detected via HRP-conjugated anti-T7 mAb (Novagen) either after unlimited (60 min) or limited (5 min) incubation time.
iii) the extract containing the c-Met-binding muteins was heated to 70° C. for 1 hour.
iv) Biotinylated c-Met receptor (R&D Systems, 2.5 μg/ml) was captured on neutravidin plates. Mutein extracts were preincubated with high excess (1 μM) of purified c-Met specific mutein S244.2-H08 (SEQ NO.: 4) from Example 5 as a competitor for target binding. Binding of expressed c-Met specific muteins was detected via HRP-conjugated anti-T7 mAb (Novagen).

A result from such a screen is depicted in FIG. 8. A large number of muteins selected as described in Example 12 and 13 were identified having improved affinity for c-Met receptor as compared to the mutein S225.4-K24 (SEQ ID NO.:1) which served as the basis for affinity maturation. Using this approach the muteins S261.1-L12, S261.1-J01, S261.1-L17 (SEQ ID NOs.:32-34) were identified. The sequences of S261.1-L12, S261.1-J01, S261.1-L17 are also depicted in FIG. 9 together with the sequence of S225.4-K24 (SEQ NO.: 1) and S244.2-H08 (SEQ NO.: 4) which is a mutein derived from error prone maturation as described in Example 5.

Example 12

Production of c-Met Receptor-Binding Muteins in a His-Tagged Format

Periplasmatic production via fermenter cultivation in a 0.75 l bioreactor was essentially performed according to Example 6 with the modification that the respective mutein is encoded on expression vector pTLPC47 (FIG. 10) instead of pTLPC10. Vector elements of pTLPC47 are identical to pTLPC10 with the modification that pTLPC47 codes for a Tlc mutein which is C-terminally fused to a Hexa-His tag (SEQ ID NO: 55) and the N-terminally fused T7-tag is removed.

The mutein was purified from the periplasmic fraction in a single step chromatographic protocol with Ni-NTA sepharose (GE) using a column of appropriate bed volume and suitable equipment according to the manufacturers' recommendations.

To achieve higher purity and to remove any aggregated recombinant protein, a gel filtration the muteins was finally carried out on a Superdex 75 HR 10/30 column (24-ml bed volume, Amersham Pharmacia Biotech) in the presence of PBS buffer. The monomeric protein fractions were pooled, checked for purity by SDS-PAGE, and used for further biochemical characterization.

Example 13

Affinity Measurement Using Surface-Plasmon-Resonance Spectroscopy (SPR)

Affinity measurements were performed essentially as described in Example 7.

Results from the affinity measurements employing S261.1-L12, S261.1-J01, S261.1-L17 (SEQ ID NOs.:32-34) and S244.2-H08 (SEQ NO.: 4) which is a mutein derived from error prone maturation described in Example 4 and 5 are are summarized in Table IV.

TABLE IV

Affinity improvement of selected muteins from second affinity maturation as described in Examples 10 and 11 compared to mutein S244.2-H08 from first affinity maturation cycle determined by SPR.

| Clone name | Kon [$10^4$ M−1 s−1] | Koff [$10^{-4}$ s−1] | KD [nM] |
|---|---|---|---|
| S261.1-L17 | 5.38 | 1.39 | 2.6 |
| S261.1-L12 | 2.7 | 0.66 | 2.4 |
| S261.1-J01 | 2.86 | 0.65 | 2.3 |
| S244.2-H08 | 1.8 | 2.58 | 14 |

Example 14

Affinity Ranking of Lipocalin Muteins on Intact Cells by Flow Cytometry

Lipocalin muteins were titrated on HT-29 cells (ATCC) essentially as described in Example 8.

Titration curves from which EC50 values for S261.1-L12, S261.1-J01, S261.1-L17 (SEQ ID NOs.:32-34) were determined are depicted in FIG. 11 and calculated EC50 values are summarized in Table V.

TABLE V

EC50 values of selected muteins of the invention for c-Met receptor as determined by FACS titration on HT-29 cells.

| Clone | EC50 [nM] |
|---|---|
| S261.1-L12 | 2.3 |
| S261.1-J01 | 8.5 |
| S261.1-L17 | 2.8 |

Example 15

Identification of Non-Antagonistic Binding Mode of c-Met Receptor-Specific Mutein Using an HGF Competition ELISA The mode of the interaction between HGF (Hepatocyte-growth factor, R&D Systems) and c-Met receptor by the selected c-Met specific muteins was evaluated in a competition ELISA. Therefore, a constant concentration of 2.5 µg/ml c-Met receptor-Fc (R&D Systems) was captured via anti-human IgG-Fc specific mAb (Jackson Immuno Research) which was immobilized on the surface of a polystyrol plate before. In the following the target was incubated for 1 hour at room temperature with a dilution series of c-Met-specific mutein starting from 100 nM in a two step dilution series and binding takes place either in absence or presence of 300 nM HGF as competitor. Bound c-Met receptor specific mutein was detected using polyclonal biotinylated anti-lipocalin 1 antibody (R&D Systems) and bound HGF was detected using polyclonal anti-HGF-bio antibody (R&D Systems). In both cases HRP-conjugated Extravidin (Sigma) was employed as secondary detection reagent.

Result from measurement employing the mutein S261.1-L7 (SEQ NO.:34) serve as an example and is depicted in FIG. 12. $K_D$ values determined from mutein titration curves are summarized in Table VI.

TABLE VI

Non-antagonistic ability and affinities for c-Met receptor of selected tear lipocalin mutein S261.1-L17 of the invention as determined by competition ELISA.

| clone | KD (nM) − HGF | KD (nM) + HGF |
|---|---|---|
| S261.1-L17 | 1.9 | 2.5 |

Example 16

Determination of Thermal Denaturation for c-Met-Binding Muteins by Use of CD Spectroscopy Circular dichroism measurements were performed essentially as described in Example 14 of the International patent application WO2006/056464, with the modification that the wavelength used was 230 nM and the mutein concentration was 250 µg/ml. The melting temperatures $T_m$ of the tear lipocalin muteins S261.1-L12, S261.1-J01, S261.1-L17 (SEQ ID NOs.:32-34) and S244.2-H08 (SEQ ID NO.: 4) are summarized in Table VI.

TABLE VI

Melting temperatures of selected muteins of the invention for c-Met receptor as determined by circular dichroism measurements.

| clone | Tm [° C.] |
|---|---|
| S261.1-L12 | 63.2 |
| S261.1-J01 | 59 |
| S261.1-L17 | 64.7 |
| S244.2-H08 | 65.5 |

TABLE VII

EC50 values and standard deviations of selected muteins of the invention for c-Met receptor as determined by FACS titration on HT-29 cells.

| Clone | EC50 [nM] |
|---|---|
| S261.1-L12_C123 | 8.6 |
| S261.1-L12_C123_HYNIC | 8.3 |

Example 17

Production of c-Met-Specific Mutein S261.1-L12_C123 with Unpaired Cystein at Position 123

Preparative production of c-Met-specific mutein S261.1-L12_C123 (SEQ NO.: 35) was performed essentially as described in Example 6 with the modification that amino acid Asn 123 was changed to cystein in order to introduce an unpaired cystein for subsequent site-directed conjugations. Cystein 123 was selected according to transfer the results from cystein-screen described in Example 9 which demonstrates good expression yield and affinity compared to the original mutein S261.1-L12 (SEQ NO.: 32) without unpaired cystein.

Example 18

Site-Directed Conjugation of HYNIC to c-Met-Specific Mutein S261.1-L12_C123

Purified mutein S262.1-l12_C123 (SEQ Nr.: 35) from Example 17 was used at a concentration of 0.8 mg/ml in PBS buffer pH 7.4 and unpaired cystein was activated by addition of 100 mM TCEP (Sigma) to a final concentration of 1 mM. After 2 hours incubation at room temperature unreacted TCEP excess was removed by gelfiltration employing a NAP-5 column (GE) according to manufacturers' recommendations. 10 molar excess of HYNIC (3-N-maleimido-6-hydraziniumpyridine hydrochloride purchased from SoluLink) was added and incubated for 2 h at room temperature. To remove the unreacted HYNIC from the conjugated mutein the reaction mixture was concentrated in an Ultracentricon (Amicon) and washed at least for 5 times using appropriate volumes of PBS buffer.

Example 19

Affinity Measurements of HYNIC-Conjugated c-Met-Specific Mutein S261.1-L12_C123 on Intact Cells by Flow Cytometry c-Met-specific mutein S261.1-L12_C123 (SEQ NO.: 35) with and without conjugated HYNIC was titrated on HT-29 cells (ATCC) essentially as described in Example 8.

Titration curves from which EC50 values were determined are depicted in FIG. 13 and calculated EC50 values are summarized in Table VII.

Example 20 pH Stability of c-Met-Specific Muteins

Purified mutein S261.1-J01 from Example 12 was incubated for 60 min at different pH ranging between pH 3 and pH 9.2. After neutralization to pH 7.4 the mutein was analysed via size-exclusion chromatography by employing an analytical Superdex 75 column (GE) according to manufacturer's recommendations.

No alteration of the mutein could be detected during the incubation period as judged by HPLC-SEC, except for pH 5-6 which is the range around the pI of the mutein some degree of dimerization occurred as depicted in FIG. 14.

Example 21

Positional Saturation Mutagenesis

Site specific mutagenesis was carried out at sequence positions 26, 27 and 29 of the affinity-maturated tear lipocalin muteins L17, O24, M02, K22, A22, K15, L03, O07 and K06 in order to assess whether the binding affinity can be significantly influenced. As shown in FIG. 15, all created mutants show the essentially same affinity.

Example 22

Affinity Maturation of the Mutein S261.1-L17 Using a Site-Directed Random Approach A library of 8×10$^8$ variants based on the mutein S261.1-L17 (SEQ ID NO:34) was designed by randomization of the positions 26, 27, 29, 30, 32, 33, 34, and 79 to allow for all 20 amino acids on these positions. The library was constructed essentially as described in Example 1 of international patent application PCT/EP2007/057971, published as WO2008/015239, with the modification that for randomization the deoxynucleotides L12-1: GAAGGCCATGACGGTG-GACNNKNNKGACNNKNNKAGCNNKNN-KNNKTCGGTGA CACCCATCACC (SEQ ID NO: 50); L12-2: CACGTGAGCACCTCCGTAMNNCGTG-TATTTTCCCGGCTC (SEQ ID NO: 51); and L12-3: ACG-GAGGTGCTCACGTGGCATACATCCAGAGG (SEQ ID NO: 52) were used instead of those disclosed in PCT/EP2007/057971. Phagemid display and selection was performed employing the phagemids essentially as described in Example 3 of international patent publication WO 2005/019256 with the following modifications: The target protein (c-met receptor Fc, R&D systems) was either employed at limited concentration (40 pM and 6 pM and 1 pM) and was presented to the library as Fc-fusion protein with subsequent capture of the phage-target complex using protein G beads (Dynal) or the target was captured at limited concentrations (50 ng/ml and 10 ng/ml and 1 ng/ml) to the protein G beads first before presenting the target-bead complex to the library phagemids. C-met bound library phages were eluted under acidic and subsequently under basic conditions. Three rounds of selection were performed.

Example 23

Affinity Screening of c-Met Receptor-Binding Muteins Using High-Throughput ELISA Screening Screening was essentially performed as described in Example 5 in alternative screening setups with the following modifications:
i) monoclonal anti-T7 antibody was coated at a concentration of 5 μg/ml on a polystyrol plate and expressed muteins were captured via T7-tag prior to incubation with limited concentrations of c-met receptor-Fc (1 nM, 0.2 nM and 0.1 nM). Binding of target was detected using a HRP (horseradish peroxidase)-conjugated goat-anti human IgG-Fc specific antibody.
ii) the extract containing the c-met-binding muteins was heated to 70° C. for 1 hour prior to complex formation with c-met receptor-Fe target. In this set up the c-met receptor-Fc was captured via mouse anti human IgG-Fc specific monoclonal antibody, which is immobilized on polystyrol plates at a concentration of 5 μg/ml.

A number of muteins selected as described above were identified having improved affinity for c-met receptor as compared to the mutein S261.1-L17 (SEQ ID NO:34) which served as the basis for affinity maturation. Using this approach the muteins S318.1-C10, S318.1-N21, S318.1-L13, S318.1-A16, S318.2-I24, S318.4-M11, S318.1-G18, and S318.1-O12 (SEQ ID NOs.:42-49) were identified.

Example 24

Affinity Measurements of c-Met-Specific Muteins on Intact Cells by Flow Cytometry After expression and purification of the muteins via affinity chromatography using the Strep-Tag fused to the C-terminus of the respective mutein (cf. Example. 6) c-Met-specific muteins S318.1-C10, S318.1-L13, S318.1-A16, S318.2-I24, and S318.1-O12 (SEQ ID NO: 42, 44, 45, 46 and 49) were titrated on HT-29 cells (ATCC) essentially as described in Example 8 and their binding affinity was compared to the affinity of mutein S261.1-L17 (SEQ ID NO:34) carrying a His6-tag (SEQ ID NO: 55) at its C-terminus.

Titration curves from which EC50 values were determined are depicted in FIG. 13 and calculated EC50 values are summarized in Table VIII.

TABLE VIII

EC50 values and standard deviations of selected muteins of the invention for c-Met receptor as determined by FACS titration on HT-29 cells.

| Clone | EC50 [nM] |
|---|---|
| S318.1-C10 | 5 |
| S318.1-L13 | 25 |
| S318.2-A16 | 10 |
| S318.2-I24 | 5 |
| S318.1-O12 | 7 |
| S261.1-L17His | 17 |

Example 25

Determination of Thermal Denaturation for c-Met-Binding Muteins by Use of CD Spectroscopy Circular dichroism measurements were performed essentially as described in Example 14 of the International patent application WO2006/056464, with the modification that the wavelength used was 230 nM and the mutein concentration was 250 μg/ml. The melting temperatures $T_m$ of the tear lipocalin muteins S318.1-C10 (SEQ ID NO: 42) and S318.1-O12 (SEQ ID NO: 49) are summarized in Table IX and compared to the melting temperature of the mutein S261.1-L17 (SEQ ID NO:34) (equipped with a His6-tag (SEQ ID NO: 55)) from which they are derived from.

TABLE IX

Melting temperatures of selected muteins of the invention for c-Met receptor as determined by circular dichroism measurements.

| Clone | Tm [° C.] |
|---|---|
| S318.1-C10 | 70 |
| S318.1-O12 | 65 |
| S261.1-L17his6 ("his6" disclosed as SEQ ID NO: 55) | 65 (rounded) |

The results of Examples 24 and 25 showed that mutein S318.1-C10 has substantially the same binding affinity as the mutein S261.1-L17 which served as a basis for its generation but at the same time mutein S138.1-C10 has a higher stability than the mutein S261.1-L17.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

What is claimed is:

1. A mutein of human tear lipocalin (hTLc) having detectable binding affinity to human Met receptor tyrosine kinase (c-Met) or a domain or fragment thereof and wherein said mutein comprises at least 8 amino acid substitutions with respect to the amino acid sequence of mature human tear lipocalin (SWISSPROT DATABANK ENTRY P31025; SEQ ID NO:36), which are selected from the group consisting of Arg 26→Thr, Val, Pro, Ser, or Gly; Glu 27→Gln, Gly, Val, or Ser; Phe 28→Met, or Asp; Pro 29→Leu, Ile, Ala, or Trp; Glu 30→Leu, Gly, Arg, or Phe; Met 31→Ser; Asn 32→Leu, Arg, Val, or Gln; Leu 33→Tyr, Val, Ile, Thr, or Phe; Glu 34→Val, Arg, or Ala; Leu 56→Asn; Ile 57→Gln; Ser 58→Ile, or Val; Asp 80→Tyr; Lys 83→Ala; Glu 104→Asp; Leu 105→Thr; His 106→Trp; and Lys 108→Gly.

2. A mutein of human tear lipocalin (hTLc) having detectable binding affinity to human Met receptor tyrosine kinase (c-Met) or a domain or fragment thereof and wherein said mutein comprises at least 6 amino acid substitutions with respect to the amino acid sequence of mature human tear lipocalin (SWISSPROT DATABANK ENTRY P31025; SEQ ID NO:36), which are selected from the group consisting of Arg 26→Thr, Val, Pro, Ser, or Gly; Glu 27→Gln, Gly, Val, or Ser; Phe 28→Met, or Asp; Pro 29→Leu, Ile, Ala, or Trp; Glu 30→Leu, Gly, Arg, or Phe; Met 31→Ser; Asn 32→Leu, Arg, Val, or Gln; Leu 33→Tyr, Val, Ile, Thr, or Phe; Glu 34→Val, Arg, or Ala; Leu 56→Asn; Ile 57→Gln; Ser 58→Ile, or Val; Asp 80→Tyr; Lys 83→Ala; Glu 104→Asp; Leu 105→Thr; His 106→Trp; and Lys 108→Gly, and wherein the mutein additionally comprises at least one of the amino acid substitutions Cys 61→Ser, Cys 101→Ser, and Cys 153→Ser.

3. The mutein according to claim 1, wherein the mutein is at its N-terminus or its C-terminus fused to an enzyme, a protein or a protein domain, a peptide, a signal sequence and/or an affinity tag.

4. The mutein according to claim 1, wherein the mutein is conjugated to a conjugation partner selected from the group consisting of an organic drug molecule, an enzyme label, a toxin, a cytostatic agent, a label which can be photoactivated and which is suitable in photodynamic therapy, a pharmaceutically suitable radioactive label, a hapten, digoxigenin, biotin, a chemotherapeutic metal complex or metal, colloidal gold and a moiety that extends the serum half-life of the mutein.

5. The mutein according to claim 1, wherein the Met receptor tyrosine kinase or domain or fragment thereof is an extracellular region or domain of the human Met receptor tyrosine kinase.

6. The mutein of claim 4, wherein the toxin is selected from the group consisting of pertussis-toxin, diphtheria toxin, ricin, saporin, *pseudomonas* exotoxin, calicheamicin or a derivative thereof, a taxoid, a maytansinoid, a tubulysin and a dolastatin analogue.

7. The mutein according to claim 1, wherein the mutein does not act as an antagonist of human hepatocyte growth factor (HGF) or human scatter factor (SF).

8. The mutein according to claim 1, wherein the mutein binds an extracellular region or a domain of Met receptor with a $K_D$ selected from the group of a $K_D$ of 200 nM or less, a $K_D$ of 100 nM or less, a $K_D$ of 20 nM or less and a $K_D$ of 1 nM or less.

9. A mutein of human tear lipocalin (hTLc) having detectable binding affinity to human Met receptor tyrosine kinase (c-Met) or a domain or fragment thereof and wherein said mutein comprises at least 6 amino acid substitutions with respect to the amino acid sequence of mature human tear lipocalin (SWISSPROT DATABANK ENTRY P31025; SEQ ID NO:36), which are selected from the group consisting of Arg 26→Thr, Val, Pro, Ser, or Gly; Glu 27→Gln, Gly, Val, or Ser; Phe 28→Met, or Asp; Pro 29→Leu, Ile, Ala, or Trp; Glu 30→Leu, Gly, Arg, or Phe; Met 31→Ser; Asn 32→Leu, Arg, Val, or Gln; Leu 33→Tyr, Val, Ile, Thr, or Phe; Glu 34→Val, Arg, or Ala; Leu 56→Asn; Ile 57→Gln; Ser 58→Ile, or Val; Asp 80→Tyr; Lys 83→Ala; Glu 104→Asp; Leu 105→Thr; His 106→Trp; and Lys 108→Gly, and further comprising at least one amino acid substitution selected from the group consisting of Thr 37→Ser; Met 39→Ile, or Leu; Asn 48→Ser; Lys 52→Thr, or Met; Met 55→Leu; Lys 65→Arg, or Leu; Ala 79→Leu, or Ser; Ala 86→Thr; and Ile 89→Ser, Gln, Thr, or His.

10. The mutein according to claim 1, wherein the mutein comprises one of the following sets of amino acid substitutions:
  a) Arg 26→Thr; Glu 27→Gln; Glu 30→Leu; Met 31→Ser; Asn 32→Leu; Leu 33→Tyr; Glu 34→Val; Leu 56→Asn; Ile 57→Gln; Asp 80→Tyr; Lys 83→Ala; Glu 104→Asp; Leu 105→Thr; His 106→Trp; and Lys 108→Gly
  b) Met 31→Leu 56→Asn; Ile 57→Gln; Asp 80→Tyr; Lys 83→Ala; Glu 104→Asp; Leu 105→Thr; His 106→Trp; and Lys 108→Gly
  c) Cys 61→Ser; Cys 101→Ser; Arg 111→Pro; Lys 114→Trp; and Cys 153→Ser.

11. The mutein of claim 1, wherein the mutein comprises one of the following sets of amino acid substitutions:
  (1) Arg 26→Thr; Glu 27→Gin: Phe 28→Met; Glu 30→Leu; Met 31→Ser; Asn 32→Leu; Leu 33→Tyr; Glu 34→Val; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly;
  (2) Arg 26→Thr; Glu 27→Gln; Phe 28→Asp; Glu 30→Leu; Met 31→Ser; Asn 32→Leu; Leu 33→Tyr; Glu 34→Val; Leu 56→Asn; Ile 57→Gln; Ser 58→Val; Asp 80→Tyr; Lys 83→Ala; Glu 104→Asp; Leu 105→Thr; His 106→Trp; and Lys 108→Gly;
  (3) Arg 26→Thr; Glu 27→Gln; Phe 28→Asp; Glu 30→Leu; Met 31→Ser; Asn 32→Leu; Leu 33→Tyr; Glu 34→Val; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly;
  (4) Arg 26→Val; Glu 27→Gly; Phe 28→Asp; Pro 29→Leu; Glu 30→Gly; Met 31→Ser; Asn 32→Arg; Leu 33→Val; Glu 34→Val; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly;
  (5) Arg 26→Pro; Glu 27→Gly; Phe 28→Asp; Pro 29→Ile; Glu 30→Arg; Met 31→Ser; Asn 32→Leu; Leu 33→Ile; Glu 34→Val; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly;
  (6) Arg 26→Ser; Phe 28→Asp; Pro 29→Ala; Glu 30→Phe; Met 31→Ser; Asn 32→Val; Leu 33→Thr; Glu 34→Val; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly;
  (7) Arg 26→Val; Glu 27→Val; Phe 28→Asp; Pro 29→Trp; Glu 30→Arg; Met 31→Ser; Asn 32→Gln; Leu 33→Val; Glu 34→Arg; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly; and
  (8) Arg 26→Gly; Glu 27→Ser; Phe 28→Asp; Pro 29→Trp; Met 31→Ser; Asn 32→Val; Leu 33→Phe; Glu 34→Ala; Leu 56→Asn; Ile 57→Gln; Ser 58→Ile; Asp 80→Tyr; Lys 83→Ala; Glu 104→Asp; Leu 105→Thr; His 106→Trp; and Lys 108→Gly.

12. A mutein of human tear lipocalin (hTLc) having detectable binding affinity to human Met receptor tyrosine kinase (c-Met) or a domain or fragment thereof and wherein said mutein comprises at least 6 amino acid substitutions with respect to the amino acid sequence of mature human tear lipocalin (SWISSPROT DATABANK ENTRY P31025; SEQ ID NO:36), which are selected from the group consisting of Arg 26→Thr, Val, Pro, Ser, or Gly; Glu 27→Gln, Gly, Val, or Ser; Phe 28→Met, or Asp; Pro 29→Leu, Ile, Ala, or Trp; Glu 30→Leu, Gly, Arg, or Phe; Met 31→Ser; Asn 32→Leu, Arg, Val, or Gln; Leu 33→Tyr, Val, Ile, Thr, or Phe; Glu 34→Val, Arg, or Ala; Leu 56→Asn; Ile 57→Gln; Ser 58→Ile, or Val; Asp 80→Tyr; Lys 83→Ala; Glu 104→Asp; Leu 105→Thr; His 106→Trp; and Lys 108→Gly, and further comprising at least one of the mutations relative to the sequence of the mature wild-type selected from the group consisting of Thr 40→Cys; Glu 73→Cys; Arg 90→Cys, Asp 95→Cys, Lys 121→Cys, Asn 123→Cys and Glu 131→Cys.

13. A mutein of human tear lipocalin (hTLc) having detectable binding affinity to human Met receptor tyrosine kinase (c-Met) or a domain or fragment thereof, wherein said mutein has an amino acid sequence set for in SEQ ID NO: 32-35, SEQ ID NO: 4-9, SEQ ID NO: 22-26, SEQ ID NO: 32-35 or SEQ ID NO: 37-49.

14. The mutein of claim 1 being stable within a pH in the range of about 2.5 to about 9.5.

15. A pharmaceutical composition comprising a mutein of human tear lipocalin as defined in claim 1 and a pharmaceutically acceptable excipient.

16. A method for producing a mutein of human tear lipocalin as defined in claim 1, wherein the mutein is produced starting from the nucleic acid encoding the mutein by means of genetic engineering methods in a bacterial or eukaryotic host organism and is isolated from this host organism or its culture.

17. A method of in vitro detecting human Met receptor tyrosine kinase (Met) or a domain or fragment thereof, comprising:
  a) contacting a mutein as defined in claim 1 with a sample suspected of containing human Met receptor tyrosin kinase (Met) or a domain or fragment thereof under suitable conditions, thereby allowing formation of a complex between the mutein and human Met receptor tyrosin kinase (Met) or a domain or fragment thereof, and
  b) detecting the complexed mutein by a suitable signal.

18. The mutein according to claim 1, wherein the mutein comprises at least 10 amino acid substitutions with respect to the amino acid sequence of the mature human tear lipocalin (SWISSPROT DATABANK ENTRY P31025; SEQ ID NO:36), which are selected from the group consisting of Arg 26→Thr, Val, Pro, Ser, or Gly; Glu 27→Gln, Gly, Val, or Ser; Phe 28→Met, or Asp; Pro 29→Leu, Ile, Ala, or Trp; Glu 30→Leu, Gly, Arg, or Phe; Met 31→Ser; Asn 32→Leu, Arg, Val, or Gln; Leu 33→Tyr, Val, Ile, Thr, or Phe; Glu 34→Val, Arg, or Ala; Leu 56→Asn; Ile 57→Gln; Ser 58→Ile, or Val; Asp 80→Tyr; Lys 83→Ala; Glu 104→Asp; Leu 105Thr; His 106→Trp; and Lys 108→Gly.

19. The mutein according to claim 1, wherein the mutein comprises at least 12 amino acid substitutions with respect to the amino acid sequence of the mature human tear lipocalin (SWISSPROT DATABANK ENTRY P31025; SEQ ID NO:36), which are selected from the group consisting of Arg 26→Thr, Val, Pro, Ser, or Gly; Glu 27→Gln, Gly, Val, or Ser; Phe 28→Met, or Asp; Pro 29→Leu, Ile, Ala, or Trp; Glu 30→Leu, Gly, Arg, or Phe; Met 31→Ser; Asn 32→Leu, Arg, Val, or Gln; Leu 33→Tyr, Val, Ile, Thr, or Phe; Glu 34→Val, Arg, or Ala; Leu 56→Asn; Ile 57→Gln; Ser 58→Ile, or Val; Asp 80→Tyr; Lys 83→Ala; Glu 104→Asp; Leu 105→Thr; His 106→Trp; and Lys 108→Gly.

20. The mutein according to claim 1, wherein the mutein comprises at least 14 amino acid substitutions with respect to the amino acid sequence of the mature human tear lipocalin (SWISSPROT DATABANK ENTRY P31025; SEQ ID NO:36), which are selected from the group consisting of Arg 26→Thr, Val, Pro, Ser, or Gly; Glu 27→Gln, Gly, Val, or Ser; Phe 28→Met, or Asp; Pro 29→Leu, Ile, Ala, or Trp; Glu 30→Leu, Gly, Arg, or Phe; Met 31→Ser; Asn 32→Leu, Arg, Val, or Gln; Leu 33→Tyr, Val, Ile, Thr, or Phe; Glu 34→Val, Arg, or Ala; Leu 56→Asn; Ile 57→Gln; Ser 58→Ile, or Val; Asp 80→Tyr; Lys 83→Ala; Glu 104→Asp; Leu 105→Thr; His 106→Trp; and Lys 108→Gly.

21. The mutein according to claim 1, wherein the mutein comprises at least 16 amino acid substitutions with respect to the amino acid sequence of the mature human tear lipocalin (SWISSPROT DATABANK ENTRY P31025; SEQ ID NO:36), which are selected from the group consisting of Arg 26→Thr, Val, Pro, Ser, or Gly; Glu 27→Gln, Gly, Val, or Ser; Phe 28→Met, or Asp; Pro 29→Leu, Ile, Ala, or Trp; Glu 30→Leu, Gly, Arg, or Phe; Met 31→Ser; Asn 32→Leu, Arg, Val, or Gln; Leu 33→Tyr, Val, Ile, Thr, or Phe; Glu 34→Val, Arg, or Ala; Leu 56→Asn; Ile 57→Gln; Ser 58→Ile, or Val; Asp 80→Tyr; Lys 83→Ala; Glu 104→Asp; Leu 105→Thr; His 106→Trp; and Lys 108→Gly.

22. The mutein according to claim 1, wherein the mutein comprises at least 17 amino acid substitutions with respect to the amino acid sequence of the mature human tear lipocalin (SWISSPROT DATABANK ENTRY P31025; SEQ ID NO:36), which are selected from the group consisting of Arg 26→Thr, Val, Pro, Ser, or Gly; Glu 27→Gln, Gly, Val, or Ser; Phe 28→Met, or Asp; Pro 29→Leu, Ile, Ala, or Trp; Glu 30→Leu, Gly, Arg, or Phe; Met 31→Ser; Asn 32→Leu, Arg, Val, or Gln; Leu 33→Tyr, Val, Ile, Thr, or Phe; Glu 34→Val, Arg, or Ala; Leu 56→Asn; Ile 57→Gln; Ser 58→Ile, or Val; Asp 80→Tyr; Lys 83→Ala; Glu 104→Asp; Leu 105→Thr; His 106→Trp; and Lys 108→Gly.

* * * * *

SEQUENCE LISTING

<160> NUMBER OF SEQ ID NOS: 71

<210> SEQ ID NO 1
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S225.4-K24)

<400> SEQUENCE: 1

```
Ala Ser Asp Glu Glu Ile Gln Asp Val Ser Gly Thr Trp Tyr Leu Lys
1               5                   10                  15

Ala Met Thr Val Asp Thr Gln Met Pro Leu Ser Leu Tyr Val Ser Val
            20                  25                  30

Thr Pro Met Thr Leu Thr Thr Leu Glu Gly Gly Asn Leu Glu Ala Lys
        35                  40                  45

Val Thr Met Asn Gln Ile Gly Arg Ser Gln Glu Val Lys Ala Val Leu
    50                  55                  60

Glu Lys Thr Asp Glu Pro Gly Lys Tyr Thr Ala Tyr Gly Gly Ala His
65                  70                  75                  80

Val Ala Tyr Ile Ile Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide primer TL50bio (assembly 5')

<400> SEQUENCE: 2
tatctgaagg ccatgacggt ggac                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide primer TL51bio (assembly 3')

<400> SEQUENCE: 3
tgcccacgag ccacacccct ggga                                          24

<210> SEQ ID NO 4
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S244.2-H08)

<400> SEQUENCE: 4

```
Ala Ser Asp Glu Glu Ile Gln Asp Val Ser Gly Thr Trp Tyr Leu Lys
1               5                   10                  15

Ala Met Thr Val Asp Thr Gln Met Pro Leu Ser Leu Tyr Val Ser Val
                20                  25                  30

Thr Pro Ile Thr Leu Thr Thr Leu Glu Gly Gly Ser Leu Glu Ala Thr
            35                  40                  45

Val Thr Leu Asn Gln Ile Gly Arg Ser Gln Glu Val Arg Ala Val Leu
        50                  55                  60

Glu Lys Thr Asp Glu Pro Gly Lys Tyr Thr Ala Tyr Gly Gly Ala His
65                  70                  75                  80

Val Ala Tyr Ile Ser Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 5
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin mutein (S244.2-L01)

<400> SEQUENCE: 5

Ala Ser Asp Glu Glu Ile Gln Asp Val Ser Gly Thr Trp Tyr Leu Lys
1               5                   10                  15

Ala Met Thr Val Asp Thr Gln Thr Pro Leu Ser Leu Tyr Val Ser Val
                20                  25                  30

Thr Pro Ile Thr Leu Thr Thr Leu Glu Gly Gly Asn Leu Glu Ala Glu
            35                  40                  45

Val Thr Leu Asn Gln Val Gly Arg Ser Gln Glu Val Arg Ala Val Leu
        50                  55                  60

Glu Lys Thr Asp Glu Pro Gly Lys Tyr Thr Ala Tyr Gly Gly Ala His
65                  70                  75                  80

Val Ala Tyr Ile Ile Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 6
<211> LENGTH: 152
<212> TYPE: PRT
<213> ORGANISM: Artificial Sequence
<220> FEATURE:
<223> OTHER INFORMATION: Description of Artificial Sequence: Synthetic
```

Mutein of human tear lipocalin mutein (S244.4-N05)

<400> SEQUENCE: 6

Ala Ser Asp Glu Glu Ile Gln Asp Val Ser Gly Thr Trp Tyr Leu Lys
1               5                   10                  15

Ala Met Thr Val Asp Pro Gln Met Pro Leu Ser Leu Tyr Val Ser Val
            20                  25                  30

Thr Pro Met Thr Leu Thr Thr Leu Glu Gly Gly Asn Leu Glu Ala Glu
        35                  40                  45

Val Thr Leu Asn Gln Val Gly Arg Ser Gln Glu Val Arg Ala Val Leu
    50                  55                  60

Glu Lys Thr Asp Glu Pro Gly Lys Tyr Thr Ala Tyr Gly Gly Ala His
65                  70                  75                  80

Val Ala Tyr Ile Thr Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 7
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin mutein (S244.5-J05)

<400> SEQUENCE: 7

Ala Ser Asp Glu Glu Ile Gln Asp Val Ser Gly Thr Trp Tyr Leu Lys
1               5                   10                  15

Ala Met Thr Val Asp Thr Gln Met Pro Leu Ser Leu Tyr Val Ser Val
            20                  25                  30

Thr Pro Met Thr Leu Thr Thr Leu Glu Gly Gly Asn Leu Glu Ala Glu
        35                  40                  45

Val Thr Leu Asn Gln Ile Gly Arg Ser Gln Glu Val Arg Ala Val Leu
    50                  55                  60

Glu Lys Thr Asp Glu Pro Gly Arg Tyr Thr Ala Tyr Gly Gly Ala His
65                  70                  75                  80

Val Ala Tyr Ile Thr Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 8
<211> LENGTH: 152
<212> TYPE: PRT

<213> ORGANISM: Artificial Sequence
<220> FEATURE:
<223> OTHER INFORMATION: Description of Artificial Sequence: Synthetic
      Mutein of human tear lipocalin mutein (S244.8-I20)

<400> SEQUENCE: 8

Ala Ser Asp Glu Glu Ile Gln Asp Val Ser Gly Thr Trp Tyr Leu Lys
1               5                   10                  15

Ala Met Thr Val Asp Thr Gln Met Pro Leu Ser Leu Tyr Val Ser Val
                20                  25                  30

Thr Pro Ile Thr Leu Thr Ala Leu Glu Gly Gly Asn Leu Glu Ala Glu
            35                  40                  45

Val Thr Leu Asn Gln Val Gly Arg Ser Gln Glu Val Lys Ala Val Leu
    50                  55                  60

Glu Lys Thr Asp Glu Pro Gly Arg Tyr Thr Ala Tyr Gly Gly Ala His
65                  70                  75                  80

Val Ala Tyr Ile Thr Arg Ser His Val Lys Asp His Tyr Ile Phe Tyr
                85                  90                  95

Ser Glu Gly Asp Thr Trp Gly Gly Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 9
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin mutein (S244.8-I07)

<400> SEQUENCE: 9

Ala Ser Asp Glu Glu Ile Gln Asp Val Ser Gly Thr Trp Tyr Leu Lys
1               5                   10                  15

Ala Met Thr Val Asp Thr Gln Val Pro Leu Ser Leu Tyr Val Ser Val
                20                  25                  30

Thr Pro Ile Thr Leu Thr Thr Leu Glu Gly Gly Asn Leu Glu Ala Glu
            35                  40                  45

Val Thr Met Asn Gln Ile Gly Arg Ser Gln Glu Val Arg Ala Val Leu
    50                  55                  60

Glu Lys Thr Asp Glu Pro Gly Arg Tyr Thr Ala Tyr Gly Gly Ala His
65                  70                  75                  80

Val Ala Tyr Ile Thr Arg Ser His Val Lys Asp His Tyr Ile Phe Tyr
                85                  90                  95

Ser Glu Gly Asp Thr Trp Gly Gly Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide primer H08_T40C forward

<400> SEQUENCE: 10
cgtctcggta acacccatat gcctcacgac cctggaaggg                40

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      Oligonucleotide primer H08_T40C reverse

<400> SEQUENCE: 11
cccttccagg gtcgtgaggc atatgggtgt taccgagacg                40

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide primer H08_D95C forward

<400> SEQUENCE: 12
caggtcgcac gtgaagtgcc actacatctt ttactctgag gg             42

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide primer H08_D95C reverse

<400> SEQUENCE: 13
ccctcagagt aaaagatgta gtggcacttc acgtgcgacc tg             42

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide primer H08_R90C forward

<400> SEQUENCE: 14
cgtggcatac atcagctgct cgcacgtgaa ggatcac                   37

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide primer H08_R90C reverse

<400> SEQUENCE: 15
gtgatccttc acgtgcgagc agctgatgta tgccacg                   37

<210> SEQ ID NO 16

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide primer A22_K121C forward

<400> SEQUENCE: 16
ggcagagacc cctgcaacaa cctggaagcc ttg                                33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      Oligonucleotide primer A22_K121C reverse

<400> SEQUENCE: 17
caaggcttcc aggttgttgc aggggtctct gcc                                33

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      Oligonucleotide primer A22_N123C forward

<400> SEQUENCE: 18
ggcagagacc ccaagaactg cctggaagcc ttggag                             36

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      Oligonucleotide primer A22_N123C reverse

<400> SEQUENCE: 19
ctccaaggct tccaggcagt tcttggggtc tctgcc                             36

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      Oligonucleotide primer H08_V93C forward

<400> SEQUENCE: 20
catcagcagg tcgcactgca aggatcacta catcttttac                         40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      Oligonucleotide primer H08_V93C reverse

<400> SEQUENCE: 21
gtaaaagatg tagtgatcct tgcagtgcga cctgctgatg                         40

<210> SEQ ID NO 22
<211> LENGTH: 152
```

<212> TYPE: PRT
<213> ORGANISM: Artificial Sequence
<220> FEATURE:
<223> OTHER INFORMATION: Description of Artificial Sequence: Synthetic
      Mutein of human tear lipocalin (S244.2-H08_C40)

<400> SEQUENCE: 22

Ala Ser Asp Glu Glu Ile Gln Asp Val Ser Gly Thr Trp Tyr Leu Lys
1               5                   10                  15

Ala Met Thr Val Asp Thr Gln Met Pro Leu Ser Leu Tyr Val Ser Val
                20                  25                  30

Thr Pro Ile Cys Leu Thr Thr Leu Glu Gly Gly Ser Leu Glu Ala Thr
            35                  40                  45

Val Thr Leu Asn Gln Ile Gly Arg Ser Gln Glu Val Arg Ala Val Leu
    50                  55                  60

Glu Lys Thr Asp Glu Pro Gly Lys Tyr Thr Ala Tyr Gly Gly Ala His
65                  70                  75                  80

Val Ala Tyr Ile Ser Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 23
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S244.2-H08_C123)

<400> SEQUENCE: 23

Ala Ser Asp Glu Glu Ile Gln Asp Val Ser Gly Thr Trp Tyr Leu Lys
1               5                   10                  15

Ala Met Thr Val Asp Thr Gln Met Pro Leu Ser Leu Tyr Val Ser Val
                20                  25                  30

Thr Pro Ile Thr Leu Thr Thr Leu Glu Gly Gly Ser Leu Glu Ala Thr
            35                  40                  45

Val Thr Leu Asn Gln Ile Gly Arg Ser Gln Glu Val Arg Ala Val Leu
    50                  55                  60

Glu Lys Thr Asp Glu Pro Gly Lys Tyr Thr Ala Tyr Gly Gly Ala His
65                  70                  75                  80

Val Ala Tyr Ile Ser Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Cys Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

```
<210> SEQ ID NO 24
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S244.2-H08_C95)

<400> SEQUENCE: 24

Ala Ser Asp Glu Glu Ile Gln Asp Val Ser Gly Thr Trp Tyr Leu Lys
1               5                   10                  15

Ala Met Thr Val Asp Thr Gln Met Pro Leu Ser Leu Tyr Val Ser Val
            20                  25                  30

Thr Pro Ile Thr Leu Thr Thr Leu Glu Gly Gly Ser Leu Glu Ala Thr
        35                  40                  45

Val Thr Leu Asn Gln Ile Gly Arg Ser Gln Glu Val Arg Ala Val Leu
    50                  55                  60

Glu Lys Thr Asp Glu Pro Gly Lys Tyr Thr Ala Tyr Gly Gly Ala His
65                  70                  75                  80

Val Ala Tyr Ile Ser Arg Ser His Val Lys Cys His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 25
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S244.2-H08_C90)

<400> SEQUENCE: 25

Ala Ser Asp Glu Glu Ile Gln Asp Val Ser Gly Thr Trp Tyr Leu Lys
1               5                   10                  15

Ala Met Thr Val Asp Thr Gln Met Pro Leu Ser Leu Tyr Val Ser Val
            20                  25                  30

Thr Pro Ile Thr Leu Thr Thr Leu Glu Gly Gly Ser Leu Glu Ala Thr
        35                  40                  45

Val Thr Leu Asn Gln Ile Gly Arg Ser Gln Glu Val Arg Ala Val Leu
    50                  55                  60

Glu Lys Thr Asp Glu Pro Gly Lys Tyr Thr Ala Tyr Gly Gly Ala His
65                  70                  75                  80

Val Ala Tyr Ile Ser Cys Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140
```

```
Gln Ser Glu Thr Ser Ser Pro Gly
145                 150
```

<210> SEQ ID NO 26
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S244.2-H08_C121)

<400> SEQUENCE: 26

```
Ala Ser Asp Glu Glu Ile Gln Asp Val Ser Gly Thr Trp Tyr Leu Lys
1               5                   10                  15

Ala Met Thr Val Asp Thr Gln Met Pro Leu Ser Leu Tyr Val Ser Val
                20                  25                  30

Thr Pro Ile Thr Leu Thr Thr Leu Glu Gly Gly Ser Leu Glu Ala Thr
            35                  40                  45

Val Thr Leu Asn Gln Ile Gly Arg Ser Gln Glu Val Arg Ala Val Leu
        50                  55                  60

Glu Lys Thr Asp Glu Pro Gly Lys Tyr Thr Ala Tyr Gly Gly Ala His
65                  70                  75                  80

Val Ala Tyr Ile Ser Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Cys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide primer K24_1
<220> FEATURE:
<221> NAME/KEY: modified_base
<222> LOCATION: (22)..(23)
<223> OTHER INFORMATION: a, c, g, or t

<400> SEQUENCE: 27
gccatgacgg tggacacgca gnnsccgctg agcctctac                           39

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide primer K24_2
<220> FEATURE:
<221> NAME/KEY: modified_base
<222> LOCATION: (17)..(18)
<223> OTHER INFORMATION: a, c, g, or t

<400> SEQUENCE: 28
cagggtcgtg agggtsnngg gtgtcaccga gac                                 33

-continued

```
<210> SEQ ID NO 29
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide primer K24_3
<220> FEATURE:
<221> NAME/KEY: modified_base
<222> LOCATION: (19)..(20)
<223> OTHER INFORMATION: a, c, g, or t
<220> FEATURE:
<221> NAME/KEY: modified_base
<222> LOCATION: (28)..(29)
<223> OTHER INFORMATION: a, c, g, or t
<220> FEATURE:
<221> NAME/KEY: modified_base
<222> LOCATION: (37)..(38)
<223> OTHER INFORMATION: a, c, g, or t

<400> SEQUENCE: 29
gggggcaacc tggaagccnn sgtcaccnns aaccagnnsg gccggtccca ggaggtg        57

<210> SEQ ID NO 30
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide primer K24_4
<220> FEATURE:
<221> NAME/KEY: modified_base
<222> LOCATION: (38)..(39)
<223> OTHER INFORMATION: a, c, g, or t

<400> SEQUENCE: 30
gtattttccc ggctcatcag ttttctccag gacggcsnnc acctcctggg accggcc        57

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide primer K24_5
<220> FEATURE:
<221> NAME/KEY: modified_base
<222> LOCATION: (21)..(22)
<223> OTHER INFORMATION: a, c, g, or t

<400> SEQUENCE: 31
gtgctcacgt ggcatacatc nnsaggtcgc acgtgaagga c                         41

<210> SEQ ID NO 32
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S261.1-L12)

<400> SEQUENCE: 32

Ala Ser Asp Glu Glu Ile Gln Asp Val Ser Gly Thr Trp Tyr Leu Lys
1               5                   10                  15

Ala Met Thr Val Asp Thr Gln Asp Pro Leu Ser Leu Tyr Val Ser Val
                20                  25                  30

Thr Pro Ile Thr Leu Thr Thr Leu Glu Gly Gly Asn Leu Glu Ala Met
            35                  40                  45

Val Thr Leu Asn Gln Val Gly Arg Ser Gln Glu Val Leu Ala Val Leu
```

```
                    50                  55                  60
Glu Lys Thr Asp Glu Pro Gly Lys Tyr Thr Ala Tyr Gly Gly Ala His
 65                  70                  75                  80

Val Ala Tyr Ile Gln Arg Ser His Val Lys Asp His Tyr Ile Phe Tyr
                 85                  90                  95

Ser Glu Gly Asp Thr Trp Gly Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150

<210> SEQ ID NO 33
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S261.1-J01)

<400> SEQUENCE: 33

Ala Ser Asp Glu Glu Ile Gln Asp Val Ser Gly Thr Trp Tyr Leu Lys
 1               5                  10                  15

Ala Met Thr Val Asp Thr Gln Asp Pro Leu Ser Leu Tyr Val Ser Val
                20                  25                  30

Thr Pro Leu Thr Leu Thr Thr Leu Glu Gly Gly Asn Leu Glu Ala Met
            35                  40                  45

Val Thr Leu Asn Gln Val Gly Arg Ser Gln Glu Val Leu Ala Val Leu
 50                 55                  60

Glu Lys Thr Asp Glu Pro Gly Lys Tyr Thr Ala Tyr Gly Gly Ala His
 65                 70                  75                  80

Val Ala Tyr Ile Thr Arg Ser His Val Lys Asp His Tyr Ile Phe Tyr
                 85                  90                  95

Ser Glu Gly Asp Thr Trp Gly Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150

<210> SEQ ID NO 34
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S261.1-L17)

<400> SEQUENCE: 34

Ala Ser Asp Glu Glu Ile Gln Asp Val Ser Gly Thr Trp Tyr Leu Lys
 1               5                  10                  15

Ala Met Thr Val Asp Thr Gln Asp Pro Leu Ser Leu Tyr Val Ser Val
                20                  25                  30

Ser Pro Ile Thr Leu Thr Thr Leu Glu Gly Gly Asn Leu Glu Ala Thr
```

```
                35                  40                  45
Val Thr Leu Asn Gln Ile Gly Arg Ser Gln Glu Val Leu Ala Val Leu
 50                  55                  60

Glu Lys Thr Asp Glu Pro Gly Lys Tyr Thr Ala Tyr Gly Gly Ala His
 65                  70                  75                  80

Val Ala Tyr Ile His Arg Ser His Val Lys Asp His Tyr Ile Phe Tyr
                 85                  90                  95

Ser Glu Gly Asp Thr Trp Gly Gly Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 35
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S261.1-L12_C123)

<400> SEQUENCE: 35

Ala Ser Asp Glu Glu Ile Gln Asp Val Ser Gly Thr Trp Tyr Leu Lys
  1               5                  10                  15

Ala Met Thr Val Asp Thr Gln Asp Pro Leu Ser Leu Tyr Val Ser Val
                 20                  25                  30

Thr Pro Ile Thr Leu Thr Thr Leu Glu Gly Gly Asn Leu Glu Ala Met
             35                  40                  45

Val Thr Leu Asn Gln Val Gly Arg Ser Gln Glu Val Leu Ala Val Leu
 50                  55                  60

Glu Lys Thr Asp Glu Pro Gly Lys Tyr Thr Ala Tyr Gly Gly Ala His
 65                  70                  75                  80

Val Ala Tyr Ile Gln Arg Ser His Val Lys Asp His Tyr Ile Phe Tyr
                 85                  90                  95

Ser Glu Gly Asp Thr Trp Gly Gly Pro Val Pro Gly Val Trp Leu Val
                100                 105                 110

Gly Arg Asp Pro Lys Asn Cys Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 36
<211> LENGTH: 158
<212> TYPE: PRT
<213> ORGANISM: Homo sapiens
<220> FEATURE:
<223> OTHER INFORMATION: Human tear lipocalin

<400> SEQUENCE: 36

His His Leu Leu Ala Ser Asp Glu Glu Ile Gln Asp Val Ser Gly Thr
  1               5                  10                  15

Trp Tyr Leu Lys Ala Met Thr Val Asp Arg Glu Phe Pro Glu Met Asn
                 20                  25                  30
```

```
Leu Glu Ser Val Thr Pro Met Thr Leu Thr Thr Leu Glu Gly Gly Asn
            35                  40                  45

Leu Glu Ala Lys Val Thr Met Leu Ile Ser Gly Arg Cys Gln Glu Val
 50                  55                  60

Lys Ala Val Leu Glu Lys Thr Asp Glu Pro Gly Lys Tyr Thr Ala Asp
 65                  70                  75                  80

Gly Gly Lys His Val Ala Tyr Ile Ile Arg Ser His Val Lys Asp His
                 85                  90                  95

Tyr Ile Phe Tyr Cys Glu Gly Glu Leu His Gly Lys Pro Val Arg Gly
                100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155
```

<210> SEQ ID NO 37
<211> LENGTH: 158
<212> TYPE: PRT
<213> ORGANISM: Artificial Sequence
<220> FEATURE:
<223> OTHER INFORMATION: Description of Artificial Sequence: Synthetic
      Mutein of human tear lipocalin mutein (S244.2-L01 with His6tag)

<400> SEQUENCE: 37

```
Ala Ser Asp Glu Glu Ile Gln Asp Val Ser Gly Thr Trp Tyr Leu Lys
 1               5                  10                  15

Ala Met Thr Val Asp Thr Gln Thr Pro Leu Ser Leu Tyr Val Ser Val
            20                  25                  30

Thr Pro Ile Thr Leu Thr Thr Leu Glu Gly Gly Asn Leu Glu Ala Glu
            35                  40                  45

Val Thr Leu Asn Gln Val Gly Arg Ser Gln Glu Val Arg Ala Val Leu
 50                  55                  60

Glu Lys Thr Asp Glu Pro Gly Lys Tyr Thr Ala Tyr Gly Gly Ala His
 65                  70                  75                  80

Val Ala Tyr Ile Ile Arg Ser His Val Lys Asp His Tyr Ile Phe Tyr
                 85                  90                  95

Ser Glu Gly Asp Thr Trp Gly Gly Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly His His His His His His
145                 150                 155
```

<210> SEQ ID NO 38
<211> LENGTH: 158
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S244.2-H08 with His6tag)

<400> SEQUENCE: 38

```
Ala Ser Asp Glu Glu Ile Gln Asp Val Ser Gly Thr Trp Tyr Leu Lys
 1               5                  10                  15
```

```
Ala Met Thr Val Asp Thr Gln Met Pro Leu Ser Leu Tyr Val Ser Val
            20                  25                  30

Thr Pro Ile Thr Leu Thr Thr Leu Glu Gly Gly Ser Leu Glu Ala Thr
            35                  40                  45

Val Thr Leu Asn Gln Ile Gly Arg Ser Gln Glu Val Arg Ala Val Leu
 50                      55                  60

Glu Lys Thr Asp Glu Pro Gly Lys Tyr Thr Ala Tyr Gly Gly Ala His
 65                  70                  75                  80

Val Ala Tyr Ile Ser Arg Ser His Val Lys Asp His Tyr Ile Phe Tyr
                 85                  90                  95

Ser Glu Gly Asp Thr Trp Gly Gly Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly His His His His His His
145                 150                 155
```

```
<210> SEQ ID NO 39
<211> LENGTH: 158
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S261.1-L12 with His6tag)

<400> SEQUENCE: 39
```

```
Ala Ser Asp Glu Glu Ile Gln Asp Val Ser Gly Thr Trp Tyr Leu Lys
 1               5                  10                  15

Ala Met Thr Val Asp Thr Gln Asp Pro Leu Ser Leu Tyr Val Ser Val
            20                  25                  30

Thr Pro Ile Thr Leu Thr Thr Leu Glu Gly Gly Asn Leu Glu Ala Met
            35                  40                  45

Val Thr Leu Asn Gln Val Gly Arg Ser Gln Glu Val Leu Ala Val Leu
 50                      55                  60

Glu Lys Thr Asp Glu Pro Gly Lys Tyr Thr Ala Tyr Gly Gly Ala His
 65                  70                  75                  80

Val Ala Tyr Ile Gln Arg Ser His Val Lys Asp His Tyr Ile Phe Tyr
                 85                  90                  95

Ser Glu Gly Asp Thr Trp Gly Gly Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly His His His His His His
145                 150                 155
```

```
<210> SEQ ID NO 40
<211> LENGTH: 158
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S261.1-J01 with His6tag)

<400> SEQUENCE: 40
```

```
Ala Ser Asp Glu Glu Ile Gln Asp Val Ser Gly Thr Trp Tyr Leu Lys
1               5                   10                  15

Ala Met Thr Val Asp Thr Gln Asp Pro Leu Ser Leu Tyr Val Ser Val
                20                  25                  30

Thr Pro Leu Thr Leu Thr Thr Leu Glu Gly Gly Asn Leu Glu Ala Met
            35                  40                  45

Val Thr Leu Asn Gln Val Gly Arg Ser Gln Glu Val Leu Ala Val Leu
        50                  55                  60

Glu Lys Thr Asp Glu Pro Gly Lys Tyr Thr Ala Tyr Gly Gly Ala His
65                  70                  75                  80

Val Ala Tyr Ile Thr Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly His His His His His His
145                 150                 155

<210> SEQ ID NO 41
<211> LENGTH: 158
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S261.1-L17 with His6tag)

<400> SEQUENCE: 41

Ala Ser Asp Glu Glu Ile Gln Asp Val Ser Gly Thr Trp Tyr Leu Lys
1               5                   10                  15

Ala Met Thr Val Asp Thr Gln Asp Pro Leu Ser Leu Tyr Val Ser Val
                20                  25                  30

Ser Pro Ile Thr Leu Thr Thr Leu Glu Gly Gly Asn Leu Glu Ala Thr
            35                  40                  45

Val Thr Leu Asn Gln Ile Gly Arg Ser Gln Glu Val Leu Ala Val Leu
        50                  55                  60

Glu Lys Thr Asp Glu Pro Gly Lys Tyr Thr Ala Tyr Gly Gly Ala His
65                  70                  75                  80

Val Ala Tyr Ile His Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly His His His His His His
145                 150                 155

<210> SEQ ID NO 42
<211> LENGTH: 152
<212> TYPE: PRT
<213> ORGANISM: Artificial Sequence
<220> FEATURE:
<223> OTHER INFORMATION: Description of Artificial Sequence: Synthetic
```

Mutein of human tear lipocalin (S318.1-c10)

<400> SEQUENCE: 42

```
Ala Ser Asp Glu Glu Ile Gln Asp Val Ser Gly Thr Trp Tyr Leu Lys
1               5                   10                  15

Ala Met Thr Val Asp Thr Gln Asp Pro Leu Ser Leu Tyr Val Ser Val
            20                  25                  30

Ser Pro Ile Thr Leu Thr Thr Leu Glu Gly Gly Asn Leu Glu Ala Thr
        35                  40                  45

Val Thr Leu Asn Gln Ile Gly Arg Ser Gln Glu Val Leu Ala Val Leu
    50                  55                  60

Glu Lys Thr Asp Glu Pro Gly Lys Tyr Thr Leu Tyr Gly Gly Ala His
65                  70                  75                  80

Val Ala Tyr Ile Gln Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

<210> SEQ ID NO 43
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S318.1-n21)

<400> SEQUENCE: 43

```
Ala Ser Asp Glu Glu Ile Gln Asp Val Ser Gly Thr Trp Tyr Leu Lys
1               5                   10                  15

Ala Met Thr Val Asp Thr Gln Asp Pro Leu Ser Leu Tyr Val Ser Val
            20                  25                  30

Ser Pro Ile Thr Leu Thr Thr Leu Glu Gly Gly Asn Leu Glu Ala Thr
        35                  40                  45

Val Thr Leu Asn Gln Ile Gly Arg Ser Gln Glu Val Leu Ala Val Leu
    50                  55                  60

Glu Lys Thr Asp Glu Pro Gly Lys Tyr Thr Leu Tyr Gly Gly Ala His
65                  70                  75                  80

Val Thr Tyr Ile Gln Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

<210> SEQ ID NO 44
<211> LENGTH: 152
<212> TYPE: PRT

<213> ORGANISM: Artificial Sequence
<220> FEATURE:
<223> OTHER INFORMATION: Description of Artificial Sequence: Synthetic Mutein of human tear lipocalin (S318.1-113)

<400> SEQUENCE: 44

| Ala | Ser | Asp | Glu | Glu | Ile | Gln | Asp | Val | Ser | Gly | Thr | Trp | Tyr | Leu | Lys |
|---|---|---|---|---|---|---|---|---|---|---|---|---|---|---|---|
| 1 | | | | 5 | | | | | 10 | | | | | 15 | |

| Ala | Met | Thr | Val | Asp | Thr | Gln | Asp | Pro | Leu | Ser | Leu | Tyr | Val | Ser | Val |
|---|---|---|---|---|---|---|---|---|---|---|---|---|---|---|---|
| | | | 20 | | | | | 25 | | | | | 30 | | |

| Ser | Pro | Ile | Thr | Leu | Thr | Thr | Leu | Glu | Gly | Gly | Asn | Leu | Glu | Ala | Thr |
|---|---|---|---|---|---|---|---|---|---|---|---|---|---|---|---|
| | | | 35 | | | | | 40 | | | | | 45 | | |

| Val | Thr | Leu | Asn | Gln | Ile | Gly | Arg | Ser | Gln | Glu | Val | Leu | Ala | Val | Leu |
|---|---|---|---|---|---|---|---|---|---|---|---|---|---|---|---|
| | 50 | | | | | 55 | | | | | 60 | | | | |

| Glu | Lys | Thr | Asp | Glu | Pro | Gly | Lys | Tyr | Thr | Ser | Tyr | Gly | Gly | Ala | His |
|---|---|---|---|---|---|---|---|---|---|---|---|---|---|---|---|
| 65 | | | | | 70 | | | | | 75 | | | | | 80 |

| Val | Thr | Tyr | Ile | Gln | Arg | Ser | His | Val | Lys | Asp | His | Tyr | Ile | Phe | Tyr |
|---|---|---|---|---|---|---|---|---|---|---|---|---|---|---|---|
| | | | | 85 | | | | | 90 | | | | | 95 | |

| Ser | Glu | Gly | Asp | Thr | Trp | Gly | Gly | Pro | Val | Pro | Gly | Val | Trp | Leu | Val |
|---|---|---|---|---|---|---|---|---|---|---|---|---|---|---|---|
| | | | 100 | | | | | 105 | | | | | 110 | | |

| Gly | Arg | Asp | Pro | Lys | Asn | Asn | Leu | Glu | Ala | Leu | Glu | Asp | Phe | Glu | Lys |
|---|---|---|---|---|---|---|---|---|---|---|---|---|---|---|---|
| | | | 115 | | | | | 120 | | | | | 125 | | |

| Ala | Ala | Gly | Ala | Arg | Gly | Leu | Ser | Thr | Glu | Ser | Ile | Leu | Ile | Pro | Arg |
|---|---|---|---|---|---|---|---|---|---|---|---|---|---|---|---|
| | 130 | | | | | 135 | | | | | 140 | | | | |

| Gln | Ser | Glu | Thr | Ser | Ser | Pro | Gly |
|---|---|---|---|---|---|---|---|
| 145 | | | | | 150 | | |

<210> SEQ ID NO 45
<211> LENGTH: 152
<212> TYPE: PRT
<213> ORGANISM: Artificial Sequence
<220> FEATURE:
<223> OTHER INFORMATION: Description of Artificial Sequence: Synthetic Mutein of human tear lipocalin (S318.1-a16)

<400> SEQUENCE: 45

| Ala | Ser | Asp | Glu | Glu | Ile | Gln | Asp | Val | Ser | Gly | Thr | Trp | Tyr | Leu | Lys |
|---|---|---|---|---|---|---|---|---|---|---|---|---|---|---|---|
| 1 | | | | 5 | | | | | 10 | | | | | 15 | |

| Ala | Met | Thr | Val | Asp | Val | Gly | Asp | Leu | Gly | Ser | Arg | Val | Val | Ser | Val |
|---|---|---|---|---|---|---|---|---|---|---|---|---|---|---|---|
| | | | 20 | | | | | 25 | | | | | 30 | | |

| Thr | Pro | Ile | Thr | Leu | Thr | Thr | Leu | Glu | Gly | Gly | Asn | Leu | Glu | Ala | Thr |
|---|---|---|---|---|---|---|---|---|---|---|---|---|---|---|---|
| | | | 35 | | | | | 40 | | | | | 45 | | |

| Val | Thr | Leu | Asn | Gln | Ile | Gly | Arg | Ser | Gln | Glu | Val | Leu | Ala | Val | Leu |
|---|---|---|---|---|---|---|---|---|---|---|---|---|---|---|---|
| | 50 | | | | | 55 | | | | | 60 | | | | |

| Glu | Lys | Thr | Asp | Glu | Pro | Gly | Lys | Tyr | Thr | Leu | Tyr | Gly | Gly | Ala | His |
|---|---|---|---|---|---|---|---|---|---|---|---|---|---|---|---|
| 65 | | | | | 70 | | | | | 75 | | | | | 80 |

| Val | Ala | Tyr | Ile | Gln | Arg | Ser | His | Val | Lys | Asp | His | Tyr | Ile | Phe | Tyr |
|---|---|---|---|---|---|---|---|---|---|---|---|---|---|---|---|
| | | | | 85 | | | | | 90 | | | | | 95 | |

| Ser | Glu | Gly | Asp | Thr | Trp | Gly | Gly | Pro | Val | Pro | Gly | Val | Trp | Leu | Val |
|---|---|---|---|---|---|---|---|---|---|---|---|---|---|---|---|
| | | | 100 | | | | | 105 | | | | | 110 | | |

| Gly | Arg | Asp | Pro | Lys | Asn | Asn | Leu | Glu | Ala | Leu | Glu | Asp | Phe | Glu | Lys |
|---|---|---|---|---|---|---|---|---|---|---|---|---|---|---|---|
| | | | 115 | | | | | 120 | | | | | 125 | | |

| Ala | Ala | Gly | Ala | Arg | Gly | Leu | Ser | Thr | Glu | Ser | Ile | Leu | Ile | Pro | Arg |
|---|---|---|---|---|---|---|---|---|---|---|---|---|---|---|---|
| | 130 | | | | | 135 | | | | | 140 | | | | |

| Gln | Ser | Glu | Thr | Ser | Ser | Pro | Gly |
|---|---|---|---|---|---|---|---|
| 145 | | | | | 150 | | |

```
<210> SEQ ID NO 46
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S318.1-i24)

<400> SEQUENCE: 46

Ala Ser Asp Glu Glu Ile Gln Asp Val Ser Gly Thr Trp Tyr Leu Lys
1               5                   10                  15

Ala Met Thr Val Asp Pro Gly Asp Ile Arg Ser Leu Ile Val Ser Val
                20                  25                  30

Thr Pro Ile Thr Leu Thr Thr Leu Glu Gly Gly Asn Leu Glu Ala Thr
            35                  40                  45

Val Thr Leu Asn Gln Ile Gly Arg Ser Gln Glu Val Leu Ala Val Leu
        50                  55                  60

Glu Lys Thr Asp Glu Pro Gly Lys Tyr Thr Leu Tyr Gly Gly Ala His
65                  70                  75                  80

Val Ala Tyr Ile Gln Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 47
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S318.1-m11)

<400> SEQUENCE: 47

Ala Ser Asp Glu Glu Ile Gln Asp Val Ser Gly Thr Trp Tyr Leu Lys
1               5                   10                  15

Ala Met Thr Val Asp Ser Glu Asp Ala Phe Ser Val Thr Val Ser Val
                20                  25                  30

Thr Pro Ile Thr Leu Thr Thr Leu Glu Gly Gly Asn Leu Glu Ala Thr
            35                  40                  45

Val Thr Leu Asn Gln Ile Gly Arg Ser Gln Glu Val Leu Ala Val Leu
        50                  55                  60

Glu Lys Thr Asp Glu Pro Gly Lys Tyr Thr Leu Tyr Gly Gly Ala His
65                  70                  75                  80

Val Ala Tyr Ile Gln Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
```

<210> SEQ ID NO 48
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S318.1-g18)

<400> SEQUENCE: 48

Ala Ser Asp Glu Glu Ile Gln Asp Val Ser Gly Thr Trp Tyr Leu Lys
1               5                   10                  15

Ala Met Thr Val Asp Val Val Asp Trp Arg Ser Gln Val Arg Ser Val
                20                  25                  30

Thr Pro Ile Thr Leu Thr Thr Leu Glu Gly Gly Asn Leu Glu Ala Thr
            35                  40                  45

Val Thr Leu Asn Gln Ile Gly Arg Ser Gln Glu Val Leu Ala Val Leu
        50                  55                  60

Glu Lys Thr Asp Glu Pro Gly Lys Tyr Thr Ala Tyr Gly Gly Ala His
65                  70                  75                  80

Val Thr Tyr Ile Gln Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 49
<211> LENGTH: 152
<212> TYPE: PRT
<213> ORGANISM: Artificial Sequence
<220> FEATURE:
<223> OTHER INFORMATION: Description of Artificial Sequence: Synthetic
      Mutein of human tear lipocalin (S318.1-o12)

<400> SEQUENCE: 49

Ala Ser Asp Glu Glu Ile Gln Asp Val Ser Gly Thr Trp Tyr Leu Lys
1               5                   10                  15

Ala Met Thr Val Asp Gly Ser Asp Trp Glu Ser Val Phe Ala Ser Val
                20                  25                  30

Thr Pro Ile Thr Leu Thr Thr Leu Glu Gly Gly Asn Leu Glu Ala Thr
            35                  40                  45

Val Thr Leu Asn Gln Ile Gly Arg Ser Gln Glu Val Leu Ala Val Leu
        50                  55                  60

Glu Lys Thr Asp Glu Pro Gly Lys Tyr Thr Leu Tyr Gly Gly Ala His
65                  70                  75                  80

Val Ala Tyr Ile Gln Arg Ser His Val Lys Asp His Tyr Ile Phe Tyr
                85                  90                  95

Ser Glu Gly Asp Thr Trp Gly Gly Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg 130                 135                 140
Gln Ser Glu Thr Ser Ser Pro Gly
145                 150

<210> SEQ ID NO 50
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide primer L12_1
<220> FEATURE:
<221> NAME/KEY: modified_base
<222> LOCATION: (20)..(21)
<223> OTHER INFORMATION: a, c, g, or t
<220> FEATURE:
<221> NAME/KEY: modified_base
<222> LOCATION: (23)..(24)
<223> OTHER INFORMATION: a, c, g, or t
<220> FEATURE:
<221> NAME/KEY: modified_base
<222> LOCATION: (29)..(30)
<223> OTHER INFORMATION: a, c, g, or t
<220> FEATURE:
<221> NAME/KEY: modified_base
<222> LOCATION: (32)..(33)
<223> OTHER INFORMATION: a, c, g, or t
<220> FEATURE:
<221> NAME/KEY: modified_base
<222> LOCATION: (38)..(39)
<223> OTHER INFORMATION: a, c, g, or t
<220> FEATURE:
<221> NAME/KEY: modified_base
<222> LOCATION: (41)..(42)
<223> OTHER INFORMATION: a, c, g, or t
<220> FEATURE:
<221> NAME/KEY: modified_base
<222> LOCATION: (44)..(45)
<223> OTHER INFORMATION: a, c, g, or t

<400> SEQUENCE: 50
gaaggccatg acgtgggacn nknnkgacnn knnkagcnnk nnknnktcgg tgacacccat    60
cacc                                                                64

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide primer L12_2
<220> FEATURE:
<221> NAME/KEY: modified_base
<222> LOCATION: (20)..(21)
<223> OTHER INFORMATION: a, c, g, or t

<400> SEQUENCE: 51
cacgtgagca cctccgtamn ncgtgtattt tcccggctc                           39

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide primer L12_3

<400> SEQUENCE: 52
acggaggtgc tcacgtggca tacatccaga gg                                  32

```
<210> SEQ ID NO 53
<211> LENGTH: 4
<212> TYPE: PRT
<213> ORGANISM: Homo sapiens

<400> SEQUENCE: 53

His His Leu Leu
1

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 54

His His His His His
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 55

His His His His His His
1               5

<210> SEQ ID NO 56
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Thr, Val, Pro, Ser, or Gly
<220> FEATURE:
<221> NAME/KEY: MOD_RES
<222> LOCATION: (27)..(27)
<223> OTHER INFORMATION: Gln, Gly, Val, or Ser
<220> FEATURE:
<221> NAME/KEY: MOD_RES
<222> LOCATION: (28)..(28)
<223> OTHER INFORMATION: Met or Asp
<220> FEATURE:
<221> NAME/KEY: MOD_RES
<222> LOCATION: (29)..(29)
<223> OTHER INFORMATION: Leu, Ile, Ala, or Trp
<220> FEATURE:
<221> NAME/KEY: MOD_RES
<222> LOCATION: (30)..(30)
<223> OTHER INFORMATION: Leu, Gly, Arg, or Phe
<220> FEATURE:
<221> NAME/KEY: MOD_RES
<222> LOCATION: (32)..(32)
<223> OTHER INFORMATION: Leu, Arg, Val, or Gln
<220> FEATURE:
<221> NAME/KEY: MOD_RES
<222> LOCATION: (33)..(33)
<223> OTHER INFORMATION: Tyr, Val, Ile, Thr, or Phe
<220> FEATURE:
<221> NAME/KEY: MOD_RES
<222> LOCATION: (34)..(34)
<223> OTHER INFORMATION: Val, Arg, or Ala
<220> FEATURE:
```

```
<221> NAME/KEY: MOD_RES
<222> LOCATION: (58)..(58)
<223> OTHER INFORMATION: Ile or Val

<400> SEQUENCE: 56

His His Leu Leu Ala Ser Asp Glu Glu Ile Gln Asp Val Ser Gly Thr
1               5                   10                  15

Trp Tyr Leu Lys Ala Met Thr Val Asp Xaa Xaa Xaa Xaa Ser Xaa
            20                  25                  30

Xaa Xaa Ser Val Thr Pro Met Thr Leu Thr Thr Leu Glu Gly Gly Asn
        35                  40                  45

Leu Glu Ala Lys Val Thr Met Asn Gln Xaa Gly Arg Cys Gln Glu Val
50                  55                  60

Lys Ala Val Leu Glu Lys Thr Asp Glu Pro Gly Lys Tyr Thr Ala Tyr
65                  70                  75                  80

Gly Gly Ala His Val Ala Tyr Ile Ile Arg Ser His Val Lys Asp His
                85                  90                  95

Tyr Ile Phe Tyr Cys Glu Gly Asp Thr Trp Gly Pro Val Arg Gly
            100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 57
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Ser Gln Glu Val
50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Ser Glu Gly Glu Leu His Gly Lys Pro Val Arg Gly
            100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Ser Ser Pro Gly Ser Asp
145                 150                 155

<210> SEQ ID NO 58
```

<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Ile or Leu
<220> FEATURE:
<221> NAME/KEY: MOD_RES
<222> LOCATION: (52)..(52)
<223> OTHER INFORMATION: Thr or Met
<220> FEATURE:
<221> NAME/KEY: MOD_RES
<222> LOCATION: (65)..(65)
<223> OTHER INFORMATION: Arg or Leu
<220> FEATURE:
<221> NAME/KEY: MOD_RES
<222> LOCATION: (79)..(79)
<223> OTHER INFORMATION: Leu or Ser
<220> FEATURE:
<221> NAME/KEY: MOD_RES
<222> LOCATION: (89)..(89)
<223> OTHER INFORMATION: Ser, Gln, Thr, or His

<400> SEQUENCE: 58

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Ser Pro Xaa Thr Leu Thr Thr Leu Glu Gly Gly Ser
        35                  40                  45

Leu Glu Ala Xaa Val Thr Leu Leu Ile Ser Gly Arg Cys Gln Glu Val
50                  55                  60

Xaa Ala Val Leu Glu Lys Thr Asp Glu Pro Gly Lys Tyr Thr Xaa Asp
65                  70                  75                  80

Gly Gly Lys His Val Thr Tyr Ile Xaa Arg Ser His Val Lys Asp His
            85                  90                  95

Tyr Ile Phe Tyr Cys Glu Gly Glu Leu His Gly Lys Pro Val Arg Gly
        100                 105                 110

Val Lys Leu Val Gly Arg Asp Pro Lys Asn Asn Leu Glu Ala Leu Glu
    115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

<210> SEQ ID NO 59
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

His His Leu Leu Ala Ser Asp Glu Glu Ile Gln Asp Val Ser Gly Thr
1               5                   10                  15

Trp Tyr Leu Lys Ala Met Thr Val Asp Thr Gln Phe Pro Leu Ser Leu
            20                  25                  30

Tyr Val Ser Val Thr Pro Met Thr Leu Thr Thr Leu Glu Gly Gly Asn
        35                  40                  45

```
Leu Glu Ala Lys Val Thr Met Asn Gln Ser Gly Arg Cys Gln Glu Val
            50                  55                  60

Lys Ala Val Leu Glu Lys Thr Asp Glu Pro Gly Lys Tyr Thr Ala Tyr
 65                  70                  75                  80

Gly Gly Ala His Val Ala Tyr Ile Ile Arg Ser His Val Lys Asp His
                 85                  90                  95

Tyr Ile Phe Tyr Cys Glu Gly Asp Thr Trp Gly Gly Pro Val Arg Gly
            100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 60
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

His His Leu Leu Ala Ser Asp Glu Glu Ile Gln Asp Val Ser Gly Thr
  1               5                  10                  15

Trp Tyr Leu Lys Ala Met Thr Val Asp Arg Glu Phe Pro Glu Ser Asn
             20                  25                  30

Leu Glu Ser Val Thr Pro Met Thr Leu Thr Thr Leu Glu Gly Gly Asn
         35                  40                  45

Leu Glu Ala Lys Val Thr Met Asn Gln Ser Gly Arg Cys Gln Glu Val
     50                  55                  60

Lys Ala Val Leu Glu Lys Thr Asp Glu Pro Gly Lys Tyr Thr Ala Tyr
 65                  70                  75                  80

Gly Gly Ala His Val Ala Tyr Ile Ile Arg Ser His Val Lys Asp His
                 85                  90                  95

Tyr Ile Phe Tyr Cys Glu Gly Asp Thr Trp Gly Gly Pro Val Arg Gly
            100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 61
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

His His Leu Leu Ala Ser Asp Glu Glu Ile Gln Asp Val Ser Gly Thr
  1               5                  10                  15

Trp Tyr Leu Lys Ala Met Thr Val Asp Arg Glu Phe Pro Glu Met Asn
             20                  25                  30
```

```
Leu Glu Ser Val Thr Pro Met Thr Leu Thr Thr Leu Glu Gly Gly Asn
         35                  40                  45

Leu Glu Ala Lys Val Thr Met Leu Ile Ser Gly Arg Ser Gln Glu Val
 50                  55                  60

Lys Ala Val Leu Glu Lys Thr Asp Glu Pro Gly Lys Tyr Thr Ala Asp
 65                  70                  75                  80

Gly Gly Lys His Val Ala Tyr Ile Ile Arg Ser His Val Lys Asp His
                 85                  90                  95

Tyr Ile Phe Tyr Ser Glu Gly Glu Leu His Gly Lys Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
130                 135                 140

Leu Ile Pro Arg Gln Ser Glu Thr Ser Ser Pro Gly Ser Asp
145                 150                 155
```

<210> SEQ ID NO 62
<211> LENGTH: 158
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

```
His His Leu Leu Ala Ser Asp Glu Glu Ile Gln Asp Val Ser Gly Thr
 1               5                  10                  15

Trp Tyr Leu Lys Ala Met Thr Val Asp Thr Gln Met Pro Leu Ser Leu
             20                  25                  30

Tyr Val Ser Val Thr Pro Met Thr Leu Thr Thr Leu Glu Gly Gly Asn
         35                  40                  45

Leu Glu Ala Lys Val Thr Met Asn Gln Ile Gly Arg Cys Gln Glu Val
 50                  55                  60

Lys Ala Val Leu Glu Lys Thr Asp Glu Pro Gly Lys Tyr Thr Ala Tyr
 65                  70                  75                  80

Gly Gly Ala His Val Ala Tyr Ile Ile Arg Ser His Val Lys Asp His
                 85                  90                  95

Tyr Ile Phe Tyr Cys Glu Gly Asp Thr Trp Gly Gly Pro Val Arg Gly
            100                 105                 110

Val Lys Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
130                 135                 140

Leu Ile Pro Arg Gln Ser Glu Thr Cys Ser Pro Gly Ser Asp
145                 150                 155
```

<210> SEQ ID NO 63
<211> LENGTH: 158
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

```
His His Leu Leu Ala Ser Asp Glu Glu Ile Gln Asp Val Ser Gly Thr
 1               5                  10                  15
```

```
Trp Tyr Leu Lys Ala Met Thr Val Asp Thr Gln Asp Pro Leu Ser Leu
             20                  25                  30

Tyr Glu Ser Val Thr Pro Met Thr Leu Thr Thr Leu Glu Gly Gly Asn
         35                  40                  45

Leu Glu Ala Lys Val Thr Met Asn Gln Val Gly Arg Cys Gln Glu Val
 50                  55                  60

Lys Ala Val Leu Glu Lys Thr Asp Glu Pro Gly Lys Tyr Thr Ala Tyr
 65                  70                  75                  80

Gly Gly Ala His Val Ala Tyr Ile Ile Arg Ser His Val Lys Asp His
                 85                  90                  95

Tyr Ile Phe Tyr Cys Glu Gly Asp Thr Trp Gly Gly Pro Val Arg Gly
             100                 105                 110

Val Lys Leu Val Gly Arg Asp Pro Lys Asn Asn Leu Glu Ala Leu Glu
         115                 120                 125

Asp Phe Glu Lys Ala Ala Gly Ala Arg Gly Leu Ser Thr Glu Ser Ile
 130                 135                 140

Leu Ile Pro Arg Gln Ser Glu Thr Cys Ser Pro Gly Ser Asp
145                 150                 155

<210> SEQ ID NO 64
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

His His Leu Leu Ala Ser Asp Glu Glu Ile Gln Asp Val Ser Gly Thr
 1               5                  10                  15

Trp Tyr Leu Lys Ala Met Thr Val Asp Thr Gln Asp Pro Leu Ser Leu
             20                  25                  30

Tyr Val Ser Val Thr Pro Met Thr Leu Thr Thr Leu Glu Gly Gly Asn
         35                  40                  45

Leu Glu Ala Lys Val Thr Met Asn Gln Ile Gly Arg Cys Gln Glu Val
 50                  55                  60

Lys Ala Val Leu Glu Lys Thr Asp Glu Pro Gly Lys Tyr Thr Ala Tyr
 65                  70                  75                  80

Gly Gly Ala His Val Ala Tyr Ile Ile Arg Ser His Val Lys Asp His
                 85                  90                  95

Tyr Ile Phe Tyr Cys Glu Gly Asp Thr Trp Gly Gly Pro Val Arg Gly
             100                 105                 110

Val Lys Leu Val Gly Arg Asp Pro Lys Asn Asn Leu Glu Ala Leu Glu
         115                 120                 125

Asp Phe Glu Lys Ala Ala Gly Ala Arg Gly Leu Ser Thr Glu Ser Ile
 130                 135                 140

Leu Ile Pro Arg Gln Ser Glu Thr Cys Ser Pro Gly Ser Asp
145                 150                 155

<210> SEQ ID NO 65
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65
```

His His Leu Leu Ala Ser Asp Glu Glu Ile Gln Asp Val Ser Gly Thr
1               5                   10                  15

Trp Tyr Leu Lys Ala Met Thr Val Asp Val Gly Asp Leu Gly Ser Arg
            20                  25                  30

Val Val Ser Val Thr Pro Met Thr Leu Thr Thr Leu Glu Gly Gly Asn
        35                  40                  45

Leu Glu Ala Lys Val Thr Met Asn Gln Ile Gly Arg Cys Gln Glu Val
    50                  55                  60

Lys Ala Val Leu Glu Lys Thr Asp Glu Pro Gly Lys Tyr Thr Ala Tyr
65                  70                  75                  80

Gly Gly Ala His Val Ala Tyr Ile Ile Arg Ser His Val Lys Asp His
                85                  90                  95

Tyr Ile Phe Tyr Cys Glu Gly Asp Thr Trp Gly Gly Pro Val Arg Gly
                100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 66
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

His His Leu Leu Ala Ser Asp Glu Glu Ile Gln Asp Val Ser Gly Thr
1               5                   10                  15

Trp Tyr Leu Lys Ala Met Thr Val Asp Pro Gly Asp Ile Arg Ser Leu
            20                  25                  30

Ile Val Ser Val Thr Pro Met Thr Leu Thr Thr Leu Glu Gly Gly Asn
        35                  40                  45

Leu Glu Ala Lys Val Thr Met Asn Gln Ile Gly Arg Cys Gln Glu Val
    50                  55                  60

Lys Ala Val Leu Glu Lys Thr Asp Glu Pro Gly Lys Tyr Thr Ala Tyr
65                  70                  75                  80

Gly Gly Ala His Val Ala Tyr Ile Ile Arg Ser His Val Lys Asp His
                85                  90                  95

Tyr Ile Phe Tyr Cys Glu Gly Asp Thr Trp Gly Gly Pro Val Arg Gly
                100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 67
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
His His Leu Leu Ala Ser Asp Glu Glu Ile Gln Asp Val Ser Gly Thr
1               5                   10                  15

Trp Tyr Leu Lys Ala Met Thr Val Asp Ser Glu Asp Ala Phe Ser Val
            20                  25                  30

Thr Val Ser Val Thr Pro Met Thr Leu Thr Thr Leu Glu Gly Gly Asn
        35                  40                  45

Leu Glu Ala Lys Val Thr Met Asn Gln Ile Gly Arg Cys Gln Glu Val
    50                  55                  60

Lys Ala Val Leu Glu Lys Thr Asp Glu Pro Gly Lys Tyr Thr Ala Tyr
65                  70                  75                  80

Gly Gly Ala His Val Ala Tyr Ile Ile Arg Ser His Val Lys Asp His
                85                  90                  95

Tyr Ile Phe Tyr Cys Glu Gly Asp Thr Trp Gly Pro Val Arg Gly
            100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

<210> SEQ ID NO 68
<211> LENGTH: 158
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
His His Leu Leu Ala Ser Asp Glu Glu Ile Gln Asp Val Ser Gly Thr
1               5                   10                  15

Trp Tyr Leu Lys Ala Met Thr Val Asp Val Asp Trp Arg Ser Gln
            20                  25                  30

Val Arg Ser Val Thr Pro Met Thr Leu Thr Thr Leu Glu Gly Gly Asn
        35                  40                  45

Leu Glu Ala Lys Val Thr Met Asn Gln Ile Gly Arg Cys Gln Glu Val
    50                  55                  60

Lys Ala Val Leu Glu Lys Thr Asp Glu Pro Gly Lys Tyr Thr Ala Tyr
65                  70                  75                  80

Gly Gly Ala His Val Ala Tyr Ile Ile Arg Ser His Val Lys Asp His
                85                  90                  95

Tyr Ile Phe Tyr Cys Glu Gly Asp Thr Trp Gly Pro Val Arg Gly
            100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

<210> SEQ ID NO 69
<211> LENGTH: 158
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 69

His His Leu Leu Ala Ser Asp Glu Glu Ile Gln Asp Val Ser Gly Thr
1               5                   10                  15

Trp Tyr Leu Lys Ala Met Thr Val Asp Gly Ser Asp Trp Glu Ser Val
            20                  25                  30

Phe Ala Ser Val Thr Pro Met Thr Leu Thr Thr Leu Glu Gly Gly Asn
        35                  40                  45

Leu Glu Ala Lys Val Thr Met Asn Gln Ile Gly Arg Cys Gln Glu Val
50                  55                  60

Lys Ala Val Leu Glu Lys Thr Asp Glu Pro Gly Lys Tyr Thr Ala Tyr
65                  70                  75                  80

Gly Gly Ala His Val Ala Tyr Ile Ile Arg Ser His Val Lys Asp His
                85                  90                  95

Tyr Ile Phe Tyr Cys Glu Gly Asp Thr Trp Gly Pro Val Arg Gly
                100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
130                 135                 140

Leu Ile Pro Arg Gln Ser Glu Thr Cys Ser Pro Gly Ser Asp
145                 150                 155

<210> SEQ ID NO 70
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Cys Leu Thr Thr Leu Glu Gly Gly Asn
        35                  40                  45

Leu Glu Ala Lys Val Thr Met Leu Ile Ser Arg Cys Gln Glu Val
50                  55                  60

Lys Ala Val Leu Glu Lys Thr Asp Cys Pro Gly Lys Tyr Thr Ala Asp
65                  70                  75                  80

Gly Gly Lys His Val Ala Tyr Ile Ile Cys Ser His Val Lys Cys His
                85                  90                  95

Tyr Ile Phe Tyr Cys Glu Gly Glu Leu His Gly Lys Pro Val Arg Gly
                100                 105                 110

Val Lys Leu Val Gly Arg Asp Pro Cys Asn Cys Leu Glu Ala Leu Glu
            115                 120                 125

Asp Phe Cys Lys Ala Ala Gly Ala Arg Gly Leu Ser Thr Glu Ser Ile
130                 135                 140

Leu Ile Pro Arg Gln Ser Glu Thr Cys Ser Pro Gly Ser Asp
145                 150                 155

<210> SEQ ID NO 71
```

```
<211> LENGTH: 152
<212> TYPE: PRT
<213> ORGANISM: Homo sapiens

<400> SEQUENCE: 71

Ala Ser Asp Glu Glu Ile Gln Asp Val Ser Gly Thr Trp Tyr Leu Lys
1               5                   10                  15

Ala Met Thr Val Asp Arg Glu Phe Pro Glu Met Asn Leu Glu Ser Val
                20                  25                  30

Thr Pro Met Thr Leu Thr Thr Leu Glu Gly Gly Asn Leu Glu Ala Lys
            35                  40                  45

Val Thr Met Leu Ile Ser Gly Arg Ser Gln Glu Val Lys Ala Val Leu
        50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Leu His Gly Lys Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150
```